United States Patent [19]

Fujiwhara et al.

[11] 4,207,111
[45] Jun. 10, 1980

[54] LIGHT-SENSITIVE SILVER HALIDE COLOR PHOTOGRAPHIC MATERIALS

[75] Inventors: Mitsuto Fujiwhara, Hachioji; Takashi Sasaki, Hino; Takashi Uchida, Hachioji, all of Japan

[73] Assignee: Konishiroku Photo Industry Co., Ltd., Nihonbashi-Muro, Japan

[21] Appl. No.: 864,229

[22] Filed: Dec. 27, 1977

[30] Foreign Application Priority Data

Dec. 28, 1976 [JP] Japan ............................ 51-158449

[51] Int. Cl.$^2$ .................. G03C 1/40; G03C 7/00
[52] U.S. Cl. ............................ 430/376; 430/385; 430/387; 430/389; 430/440; 430/471
[58] Field of Search .................. 96/100 R, 55, 56.5, 96/56, 100 N, 56.4

[56] References Cited

U.S. PATENT DOCUMENTS

| | | | |
|---|---|---|---|
| 3,432,300 | 3/1969 | Lestina et al. | 96/56 |
| 3,519,429 | 7/1970 | Lestina | 96/56 |
| 3,930,866 | 1/1976 | Oishi et al. | 96/56 |

*Primary Examiner*—J. Travis Brown
*Attorney, Agent, or Firm*—Haseltine, Lake & Waters

[57] ABSTRACT

A color photosensitive material having a support and a silver halide photosensitive layer which material includes a coupler represented by the following formulas (IV), (V) or (VI) having therein a group represented by formula (I), said coupler being capable of forming an azomethine dye on coupling with the oxidation product of an aromatic primary amine developer:

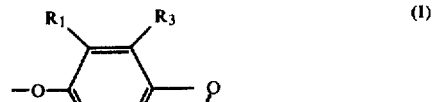

(I)

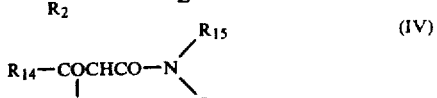

(IV)

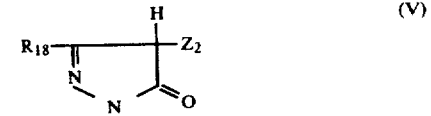

(V)

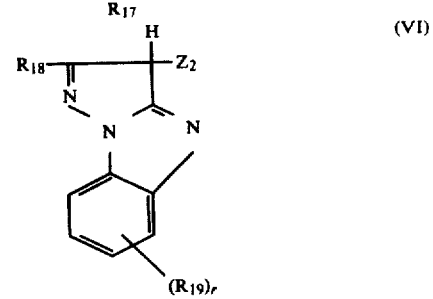

(VI)

wherein the substituents on the above formulas is herein defined, is described, said couplers capable of giving improved light fastness.

19 Claims, No Drawings

LIGHT-SENSITIVE SILVER HALIDE COLOR PHOTOGRAPHIC MATERIALS

This invention relates to light-sensitive silver halide color photographic materials and particularly is concerned with light-sensitive silver halide color photographic materials containing novel couplers capable of giving dye images improved in light fastness.

Formation of color photographic images according to the subtractive process is generally carried out by subjecting a light-sensitive silver halide color photographic material (hereinafter called "color photosensitive material") to color development by the use of an aromatic primary amine type developing agent in the presence of a cyan coupler, a magenta coupler and a yellow coupler. In that case, the silver halide particles present in the exposed color photosensitive material are reduced by the developing agent and an oxidation product of said developing agent simultaneously formed thereby reacts by coupling with the couplers to form a cyan dye, a magenta dye and a yellow dye respectively, thereby forming a photographic image.

Each coupler may be incorporated into a color photosensitive material, and generally color photosensitive materials of the type, into which the couplers can be incorporated, are called color photosensitive materials of an internal type, and color photosensitive materials which are processed after exposure with a color developing solution, into which the couplers are incorporated, are called color photosensitive materials of an external type.

The present invention is concerned with the internal type color photosensitive materials having incorporated therein the couplers.

As yellow couplers to form yellow dyes, there are used generally compounds having open chain active methylene groups. Magenta couplers used to form magenta dyes generally include compounds having closed chain active methylene groups such as a pyrazolone, pyrazolino-benzimidazole, indazolone or pyrazolotriazole nucleus, and each of such compounds forms an azomethine dye on color development. On the other hand, cyan couplers used to form cyan dyes include generally phenol type or α-naphthol type compounds, and these compounds form indoaniline type dyes on color development.

Dye images obtained from such couplers on color development are desired which are not subject to discloring or fading even when stored at high temperature and high humidity.

Such dye images are referred to above are, however, not found yet to be satisfactory their fastness to an ultraviolet ray or a visible ray. It is well known that such dye images are easily discolored or faded when irradiated with these actinic rays. Further, unreacted couplers which remain mainly in unexposed areas of the developed color photosensitive materials undergo chemical change to form the so-called yellow stain (hereinafter called "Y-stain"). Such discoloring or fading as mentioned above comes into question in the case of color image prints which are irradiated with actinic rays for a long period of time.

In order to overcome such drawbacks, various proposals have heretofore been made.

For instance, a process in which various ultraviolet absorbers are incorporated into color photographic materials (such as disclosed in such as U.S. Pat. Nos. 3,159,646, 3,004,896, 3,253,921 and 3,214,436, British Patents 991,204, 991,603 and 1,026,142 and French Pat. No. 1,585,596), a process in which fading inhibitors having phenolic hydroxyl groups are incorporated into color photographic materials (as disclosed in Japanese Patent Publication Nos. 31256/1973, 31625/1973 and 20977/1974, U.S. Pat. Nos. 3,069,262 and 2,360,290, and Japanese Laid-Open-to-Public Publication Nos. 27333/1976, 3432300/1976, 3574627/1976, 3573050/1976 and 27333/1976/.

However, there is a limit to such processes for the improvement as relying on these additives. For instance, for satisfying light fastness, relatively large amounts of such additives are required to be incorporated into color photographic materials, thereby to bring about often such disadvantages as coloration and to increase in film thickness due to the use of large amounts of additives, degradation of sharpness associated with the use thereof and so on. In addition to the improvement relying on the additives used, it is also well-known to improve light fastness by the use of couplers of various structures being selected as suitable for the purpose.

For instance, there are proposed couplers having an o-hydroxyphenylbenztriazole nucleus which is an ultraviolet absorbing group; pyrazolone type magenta couplers and phenol type cyan couplers having phenolic hydroxyl groups as stabilizing groups as disclosed in U.S. Pat. Nos. 3,519,429 and 3,880,661; and couplers containing hydroquinone diether groups as groups capable of giving light fast dyes in Japanese Laid-Open-to-Public Publication No. 20723/1975. The couplers having ultraviolet absorbing groups, however, have no effect on prevention of fading due to visible rays, though they are effective on fading due to ultraviolet rays. The couplers having stabilizing groups, on the other hand, are not sufficiently stable when contacted with such high alkali solution as the color developer and bring about side reactions. Thus, these couplers are not satisfied yet in fading prevention effect.

In this manner, various attempts to improve light fastness have heretofore been made by the use of such additives, for example, as fading inhibitors or by the selection of couplers suitable for the purpose. In comparison with indoaniline dyes obtained from phenol or α-naphthol type cyan couplers, however, azomethine dyes obtained from active methylene type yellow couplers or magenta couplers are inherently less stable in structure, and hence there are unsolved problems concerning light fastness and the like properties. Accordingly, couplers capable of forming excellent azomethine dyes are being sought, because of being used recently under further severe conditions in particular.

Properties required for photographic couplers are such that not only the dye formed thereby is excellent in stability but also the coupler is excellent in color developability, solubility in organic solvents, dispersion stability to silver halide emulsion, and has a sufficiently high color density and an absorption wavelength region within a desirable range, and that various photographic properties of a silver halide emulsion having the coupler incorporated therein are found favorable.

An object of the present invention is to provide couplers having a particularly high light fastness, said couplers being capable of satisfying various characteristics required for photographic couplers as aforesaid.

A further object of the present invention is to provide color photosensitive materials containing couplers capable of giving dye images improved in stability to light.

As a result of studies, the present inventors have found that the above-mentioned object of the present invention can be accomplished by incorporating at least one of the couplers (hereinafter called "present couplers") having therein a group represented by the following general formula [I] into a color photosensitive material, said couplers being capable of forming azomethine dyes on coupling with an aromatic primary amine compound.

General formula [I]

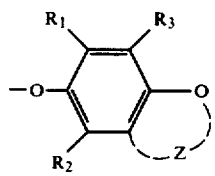

wherein $R_1$, $R_2$ and $R_3$ individually represent hydrogen, halogen (e.g. fluorine, chlorine, bromine, etc.), an alkyl group (e.g. methyl, ethyl, propyl, butyl, octyl, dodecyl, etc.), an alkenyl group (e.g. allyl, octenyl, etc.), a cycloalkyl group (e.g. cycloheptyl, cyclohexyl, etc.), an aryl group (e.g. phenyl, naphthyl, etc.), an alkoxy group (e.g. methoxy, ethoxy, butoxy, dodecyloxy, etc.), an alkenyloxy group (e.g. allyloxy, etc.), a cycloalkoxy group (e.g. cyclohexyloxy, etc.), an aryloxy group (e.g. phenoxy, etc.), an akylthio group (e.g. methylthio, ethylthio, butylthio, octylthio, etc.), an alkenylthio group (e.g. allylthio, etc.), a cycloalkylthio group (e.g. cyclohexylthio, etc.), an arylthio group (e.g. phenylthio, etc.), an acyl group (e.g. acetyl, propioloyl, octanoyl, benzoyl, cinnamoyl, etc.), an acylamino group (e.g. acetylamino, propioloylamino, benzoylamino, etc.), a diacylamino group, an acyloxy group (e.g. acetyloxy, propioloyloxy, benzoyloxy, cinnamoyloxy, etc.), a sulfonamido group (e.g. methylsulfonamide, propanesulfonamido, butanesulfonamido, octylsulfonamido, etc.) or an alkoxycarbonyl group (e.g. methoxycarbonyl, propyloxycarbonyl, octyloxycarbonyl, etc.), and Z represents an atomic group necessary for forming a chroman ring or a coumaran ring.

The group of the general formula [I] according to the present invention may be present in any position of a coupler capable of forming an azomethine dye on coupling with an aromatic primary amine compound. The coupler may have said group, for example, as a diffusion resisting group as well as a group capable of releasing, at the time when said coupler couples with an oxidation product, a color developing agent (the latter group is the so-called split off group). Further, the group of the general formula [I] may bond, either directly or through any divalent group, to the coupler.

The divalent group referred to above is preferably represented by the formula $+(Q_1)_n+(Q_2)_m$ in which n is 0 or 1 and m is 0 or 1 where $Q_1$ is an alkylene group (e.g. methylene, ethylene, trimethylene, hexamethylene, octamethylene, dodecamethylene, propylene, ethylidene, butylidene, octylidene, etc.), a cycloalkylene group (e.g. cyclohexylene), an arylene group (e.g. phenylene, naphthylene, etc.), a divalent group in which at least one an alkylene group is bonded to at least one arylene group (e.g. tolylene, xylylene, etc.), or or a divalent heterocyclic ring (e.g. a divalent heterocyclic group containing nitrogen and/or sulfur, such as isothiazole, piperadine, imidazoline, pyridazine, pyrimidine, pyrazine, triazine, pyrazole, imidazole, piperidine, thiazolin, etc.), and $Q_2$ is

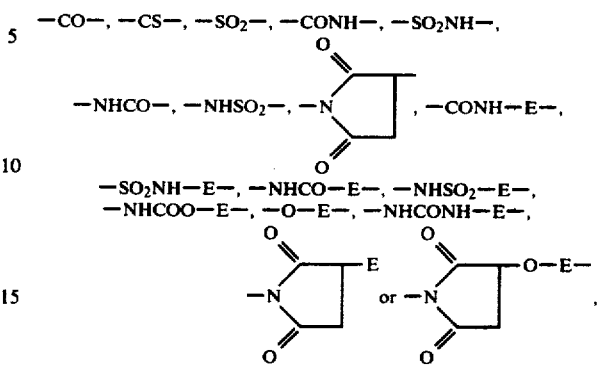

(E represents an alkylene group.).

Preferably the $Q_2$ group represents —CO—, —NHCO—,

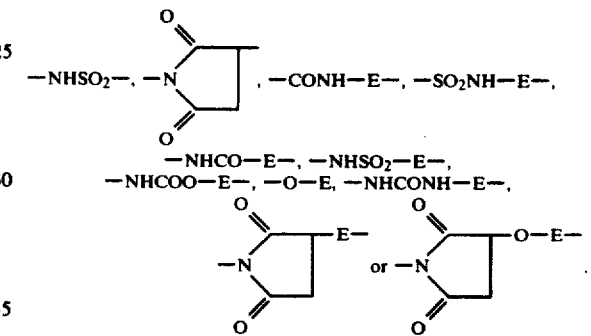

E represents preferably an alkylene group having 1~22 carbon atoms.

Of the groups represented by general formula [I], those which are useful for the present invention include such groups as represented by the following general formulas [II] and [III].

General formula [II]

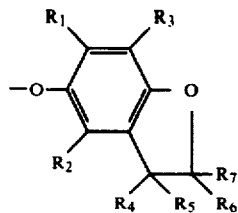

General formula [III]

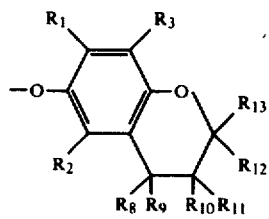

In the above-mentioned general formula [II] and [III], $R_1$, $R_2$ and $R_3$ are individually as defined in the general formula I and $R_4$, $R_5$, $R_6$, $R_7$, $R_8$, $R_9$, $R_{10}$, $R_{11}$, $R_{12}$ and $R_{13}$ individually represent hydrogen, halogen (e.g. the previously mentioned atoms), alkyl (e.g. the previously mentioned alkyls), alkoxy (e.g. the previously mentioned alkoxys), alkylthio (e.g. the previously mentioned alkylthios), alkenyl (e.g. the previously mentioned alkenyls), alkenyloxy (e.g. the previously alkenyloxys), alkenylthio (e.g. the previously mentioned alkenylthios), cycloalkyl (e.g. the previously mentioned cycloalkyls), cycloalkyloxy (e.g. the previously mentioned cycloalkyloxys), aryl (e.g. the previously mentioned aryls), aryloxy (e.g. the previously mentioned aryloxys), heterocyclic nucleus (e.g. the previously mentioned nuclei), or an amino group.

Further, $R_{12}$ and $R_{13}$ may cyclize together to form a hydrocarbon nucleus (e.g. a cyclopentane, cyclohexane, cycloheptane, cyclohexene or cyclohexadiene nucleus and so on).

Preferable as the hydrocarbon nucleus is a 5-membered or 6-membered saturated hydrocarbon nucleus (cyclopentane and cyclohexane nuclei).

Of the groups of the aforementioned general formulas [II] and [III], those which are useful in the present invention are such groups in which $R_1$, $R_2$ and $R_3$ are individually hydrogen, an alkyl group or a cycloalkyl group, $R_4$, $R_5$, $R_6$, $R_7$, $R_8$, $R_9$, $R_{10}$, $R_{11}$, $R_{12}$ and $R_{13}$ are individually a hydrogen, halogen, alkyl having 1 to 22 carbon atoms or cycloalkyl, and $R_{12}$ and $R_{13}$ cyclize together to form a 5- or 6-membered saturated hydrocarbon nucleus.

In the groups of the aforementioned general formulas [II] and [III], those in which $R_1$, $R_2$, $R_3$, $R_4$, $R_5$, $R_6$, $R_8$, $R_9$, $R_{10}$, $R_{11}$, $R_{12}$ and $R_{13}$ are individually hydrogen, or alkyl or an alkyl group having 1 to 22 carbon atoms are particularly useful in the present invention, and those in which $R_7$ is individually alkoxy, aryloxy, an amino group or a heterocyclic nucleus containing nitrogen.

In the group of the aforementioned general formulas [II] and [III], in $R_1$, $R_4$, $R_5$, $R_8$, $R_{12}$ and $R_{13}$ each are preferably lower alkyl or a lower alkyl group, especially methyl or a methyl group, and $R_2$, $R_3$, $R_6$, $R_9$, $R_{10}$ and $R_{11}$ are individually hydrogen.

Between the aforementioned general formula [II] and [III], the general formula [III] is such preferred.

The coupler of the present invention may be any as couplers as capable of forming an azomethine dye on coupling with an aromatic primary amine developer. Such couplers may be either 4-equivalent couplers having active methylene groups or 2-equivalent couplers having split-off groups at the coupling position of said couplers. The 2-equivalent couplers may be either so-called development inhibitor releasing type couplers (D.I.R. couplers) wherein the group that has split off forms a development inhibitor or colored couplers for use in so-called masking.

The coupler of the present invention includes, for example, acylacetonitrile yellow couplers, acylacetanilide yellow couplers, acylacetyl yellow couplers, 5-pyrazolone magenta couplers, indazolone magenta couplers, pyrazolinobenzimidazole magenta couplers, etc., preferably acylacetanilide yellow couplers, 5-pyrazolone magenta couplers and pyrazolinobenzimidazole magenta couplers, particularly preferably 5-pyrazolone magenta couplers and pyrazolinobenzimidazole magenta couplers. More concretely, useful couplers of the present invention include those which are represented by the following general formula [IV].

General formula [IV]

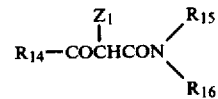

wherein $R_{14}$, $R_{15}$ and $R_{16}$ represent such groups as may be used in ordinary 4-equivalent type acylacetanilide couplers, concretely typical examples of the group represented by $R_{14}$ includes, for example, an alkyl group (e.g. methyl, isobutyl, t-butyl, t-amyl, n-hexyl, 1-methylpentyl, neopentyl, isohexyl, n-octyl, t-octyl, n-dodecyl, t-dodecyl, t-octadecyl, etc.), a terpenyl group (e.g. pinanyl, bornyl, norbonyl, etc.), a cycloalkyl group (e.g. cyclopentyl, cyclohexyl, cyclohexyl, etc.), an aryl group (e.g. phenyl, naphthyl, etc.), a heterocyclic ring (e.g. pyridyl, pyrazinyl, pyridazyl, quinonyl, thienyl, furanyl, thiazolyl, benzothiazolyl, oxazolyl, piperidyl, pyrrolyl, pyrrolinyl, tetrazolyl, thiazinyl, morpholino, furyl, benzooxazolyl, imidazolyl, benzoimidazolyl, etc.).

$R_{15}$ and $R_{16}$ are groups which may be the same or different, and typical examples of the groups include hydrogen, an alkyl group (e.g. methyl, ethyl, propyl, n-butyl, amyl, t-amyl, n-octyl, t-octyl, n-dodecyl, n-octadecyl, etc.) and an aryl group (e.g. phenyl, naphthyl, etc.). $Z_1$ represents hydrogen or a split-off group. The split-off group includes atoms or groups known to the photographic industry, such as halogen, $-OZ'$, $-OCOZ'$, $-SZ'$, $-OCONHZ'$, $-OSO_2NHZ'$, $-NHCOZ'$, $-NHSO_2Z'$, $-NHZ'$ ($Z'$ represents hydrogen, an alkyl group, an aryl group or a heterocyclic ring), $-SO_3H$, $-SCN$, an azo group, or a heterocyclic ring containing nitrogen, oxygen and/or sulfur.

Typical examples of the above-mentioned split-off group are disclosed, for example, in Japanese Laid-Open-to-Public publication Nos. 10135/1975, 91323/1975, 120334/1975, 130441/1975, 25228/1975, 37647/1976, 52828/1976 and 117422/1976, U.S. Pat. Nos. 3,617,291 and 3,227,550, and British Pat. No. 1,331,179. In the aforementioned general formula [IV], however, at least one of $R_{14}$, $R_{15}$, $R_{16}$ and and $Z_1$ is

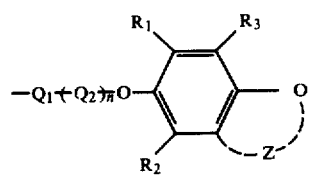

is which preferably $Q_1$ is selected from an ethylene group, an arylene group and a divalent heterocyclic ring.

In the aforementioned general formula [IV], $R_{14}$ is preferably a tertiary-alkyl group (e.g. t-butyl, t-amyl, t-hexyl, t-octyl, t-dodecyl, etc.), an aryl group (e.g. phenyl), an alkaryl group having alkyl having 1 to 15 carbon atoms (e.g. 4-methyl-phenyl, 2-methyl-phenyl, 3,5-dimethylphenyl, 4-butyl-phenyl, 4-octyl-phenyl, 4-dodecylphenyl, etc.), an alkyl group, an aryl group or an alkaryl group substituted, either directly or through a divalent group, by the group represented by the general formula [I]. Preferably, $R_{15}$ and $R_{16}$ are individually hydrogen or phenyl substituted, either directly or through the aforementioned divalent group, by halogen, an alkoxy group, a sulfonamido group, an acylamino group or the group represented by the general formula [I], and $R_{15}$ and $R_{16}$ do not simultaneously represent hydrogen.

Among the couplers represented by the general formula [IV], those which are of special usefulness in the present invention are couplers represented by the following formulas [IV-a] or [IV-b]:

General formula [IV-a]

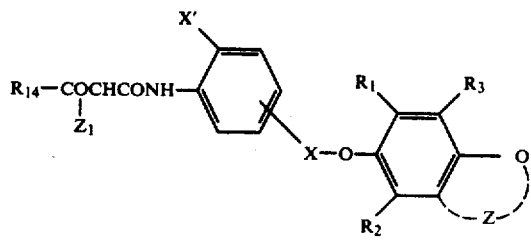

General formula [IV-b]

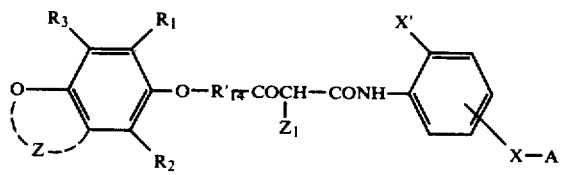

In general formulas [IV-a] and [IV-b], Z, $R_{14}$, $Z_1$, $R_1$, $R_2$ and $R_3$ are individually as defined in general formulas [I] and [IV]; X represents —NHCO—R"—, —NHSO$_2$—R"—, —COO—R'—, —NHCONH—R'—, —CONH—R'—, —SO$_2$NH—R'— or

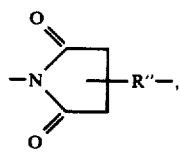

R' represents an alkylene group, an arylene group or a divalent heterocyclic ring, R" represents a simple bond or R', R'$_{14}$ represents an alkylene group, an arylene group or a divalent heterocyclic ring, A represents an alkyl group, an aryl group or a heterocyclic ring, or X' represents halogen, an alkoxy group or an aryloxy group. In general formulas [IV-a] and [IV-b], preferably an alkyl group are alkyl of having carbon atoms 1∼32.

More concretely, useful coupler residues are those which are disclosed in U.S. Pat. Nos. 2,875,057, 3,265,506, 3,664,841, 3,408,194, 3,447,928, 3,277,155 and 3,415,625, Japanese Laid-Open-to-Public publication Nos. 29432/1973, 66834/1973, 10736/1974, 122335/1974, 28834/1975 and 132926/1975, and Japanese Patent Publication No. 13576/1974.

Useful as the couplers of the present invention, moreover, are those which are represented by the following general formula [V] or [VI].
General formula [V]

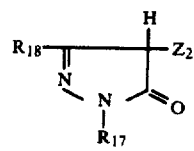

General formula [VI]

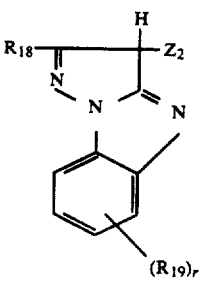

wherein $R_{17}$ and $R_{18}$ individually represent a group used in ordinary 4-equivalent couplers, and concretely $R_{17}$ includes hydrogen, an alkyl group (e.g. methyl, ethyl, n-propyl, isopropyl, n-butyl, sec-butyl-, t-butyl, n-hexyl, t-octyl, dodecyl, etc.), an alkenyl group (e.g. allyl, octenyl, etc.), a cycloalkyl group (e.g. cyclohexyl, etc.), a terpenyl group (e.g. norbornyl, etc.), an aryl group (e.g. phenyl, naphthyl, etc.), a heterocyclic ring (pyridyl, pyrazinyl, pyridazyl, quinonyl, thienyl, furyl, thiazinyl, morpholino, tetrazolyl, benzothiazolyl, thiazolyl, benzoxazolyl, oxazolyl, benzimidazolyl, imidazolyl, piperidyl, pyrrolyl, pyrrolinyl, naphthoxazolyl, etc.). A particularly useful group as represented by $R_{17}$ is phenyl substituted in at least one of the ortho positions by alkyl, alkoxy or halogen.

$R_{18}$ includes groups mentioned above in the case of $R_{17}$ such, as an alkyl group, an aryl group, a terpenyl group, heterocyclic ring, an alkoxy group, an alkenyl group, an amino group or a ureido group and the like groups.

$R_{19}$ includes hydrogen, halogen (e.g. fluorine, chlorine, bromine, etc.), an alkyl group (e.g. methyl, ethyl, propyl, butyl, etc.), an alkoxy group (e.g. methoxy, ethoxy, etc.), an acylamino group (e.g. acetamino, benzenesulfonamino, 2,4-di-t-amylphenoxyacetamino, etc.), a carbamoyl group (e.g. dodecylcarbamoyl, etc.) and a sulfamoyl group (e.g. dodecylsulfamoyl, etc.), and r represents an integer of 1 to 4, and when two or more $R_{19}$ groups are present in the same one molecule, they may be the same or different.

More concretely, useful coupler residues are those which are disclosed in U.S. Pat. Nos. 2,600,788, 3,002,653, 3,127,269, 3,311,476, 3,419,391, 3,519,429, 3,558,310, 3,684,514, 3,888,680 and 3,061,432, Japanese Patent Application Nos. 42690/1975, 134470/1975 and 156327/1975, Japanese Laid-Open-to-Public Publication Nos. 29639/1974, 111631/1974, 129538/1974 and 13041/1975, Japanese Patent Publication No. 60479/1971 and West German Pat. No. 2,156,111. $Z_2$ is as defined for $Z_1$ of the aforementioned general formula [IV].

Among the couplers represented by the general formula [V], those which are of special usefulness in the present invention are couplers represented by the following formulas [V-a] or [V-b]:
General formula [V-a]

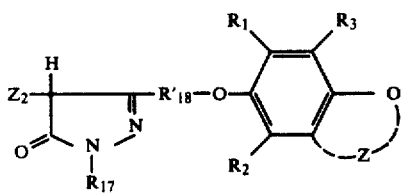

General formulas [V-b]

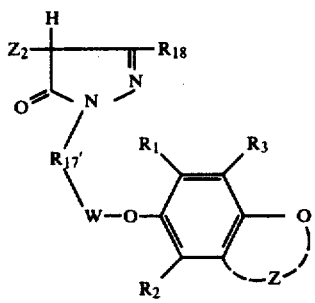

In general formulas [V-a] and [V-b], $Z_2$, $R_1$, $R_2$, $R_3$, $R_{17}$ and $R_{18}$ are individually as defined in general formulas [I], [IV-a] and [V]; $R'_{18}$ represents

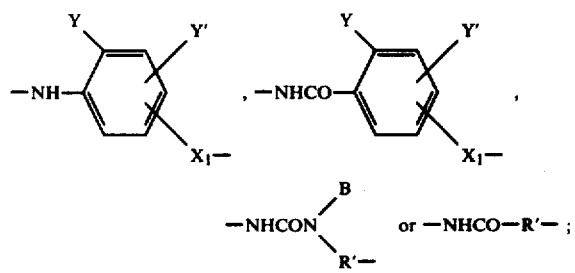

Y represents hydrogen, halogen, or alkyl group or an alkoxy group; Y' is Y; B represents hydrogen or an alkyl group; $X_1$ represent —NHCO—R'—, —NHSO$_2$—R'—, —CONH—R'—,

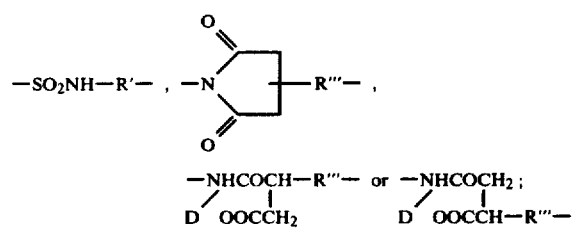

R''' represents a simple bond, —O—R'—, —S—R'—, —SO$_2$R'— or —ND—R'—; D represents hydrogen, an alkyl group, an aryl group or an acyl group; D' represent an alkyl group; R'$_{17}$ represents an alkylene group or an arylene group, or W represents a simple bond, —NH—R'—, —NHCO—R'—, —NHCONH—R'—, —O—R'— or —CONH—R'—. In the aforementioned general formula [V-b], R'$_{17}$ is preferably a phenylene group, and especially halogen-substituted phenylene.

In the aforementioned general formulas, R'$_{18}$ is preferably

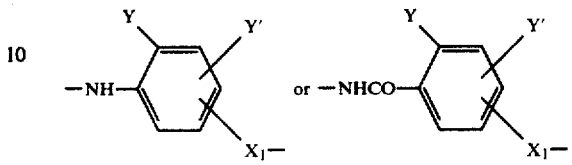

$X_1$ is preferably —NHCO—R'— or —NHSO$_2$—R'—, and R' is preferably an alkylene group.

In the aforementioned general formula [V-a], R'$_{18}$ more preferably represents

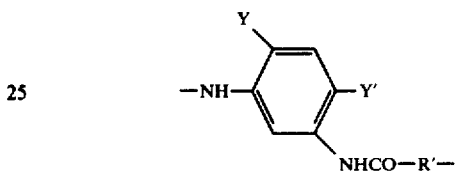

In the aforementioned general formula [V] and [VI], at least one of $R_{17}$, $R_{18}$, $R_{19}$ and $Z_2$ is the group represented by the general formula [I] or said group being bonded through the aforementioned divalent group.

In the general formulas [V] and [VI], $R_{17}$ is preferably individually a halogen-substituted phenyl, alkylphenyl or lower alkoxyphenyl group or the aforesaid group substituted, either directly or through the aforementioned divalent group, by the group represented by the general formula [I] and $R_{18}$ is an arylamino group (e.g. anilino) or arylcarbonylamino group (e.g. benzoylamino), of which the aryl moiety may be substituted, either directly or through the aforementioned divalent group, by halogen, a lower alkyl group, a lower alkoxy group or the group represented by the general formula [I].

The groups and rings in all the general formulas include the substituents as explained before. Although the substituents may be any substituents, preferred ones are one or more appropriately selected from the group consisting of halogen, cyano, hydroxy, amino, nitro, sulfo, carboxy, an alkyl group, an alkenyl group, an aryl group, a cycloalkyl group, an alkoxy group, an alkenyloxy group, an aryloxy group, an acyl group, an acyloxy group, a oxycarbonyl group, an acylamino group, a sulfamoyl group, a ureido group, a heterocyclic ring, mono- or di-alkylamino group, mono- or di-aryl amino group, a sulfonyl group, a carbamoyl group, a sulfonamido group or N-alkyl-N-aryl amino group.

Typical examples of the couplers of the present invention are exemplified below, but the couplers usable in the invention are not limited to those exemplified.

Exemplified coupler:

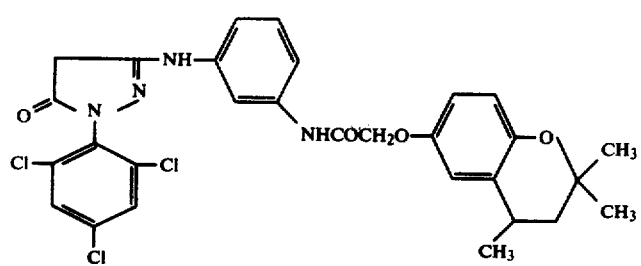 (M-1)
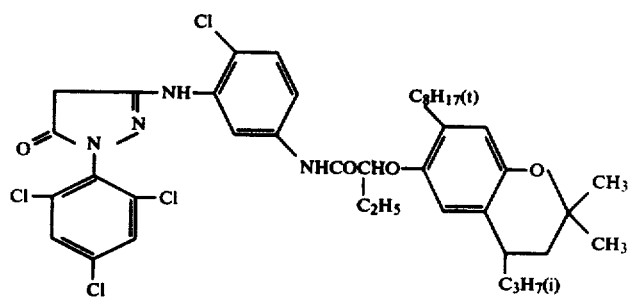 (M-2)
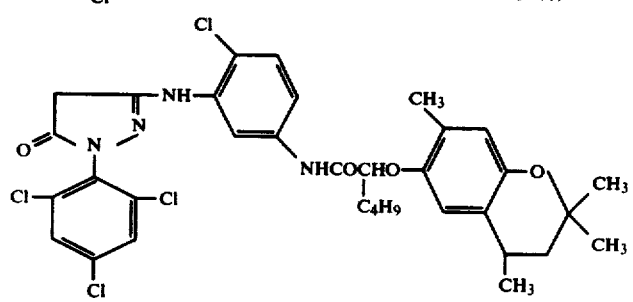 (M-3)
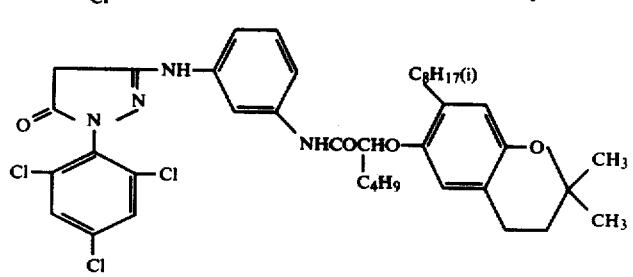 (M-4)
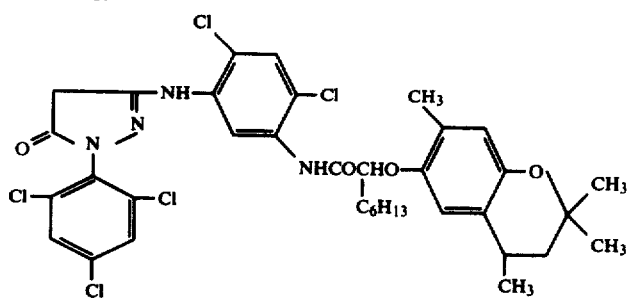 (M-5)
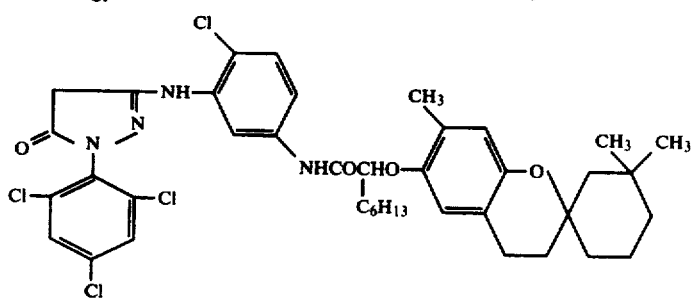 (M-6)

-continued
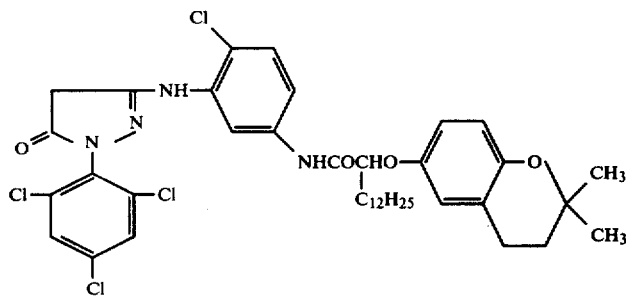 (M-7)
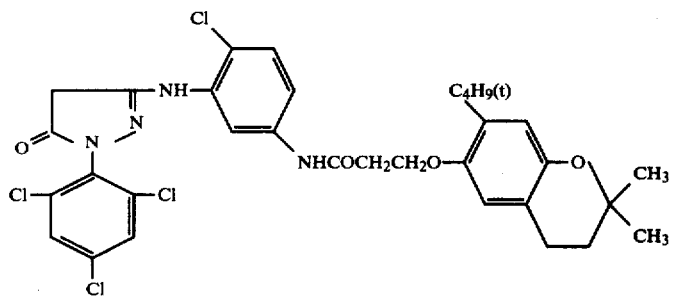 (M-8)
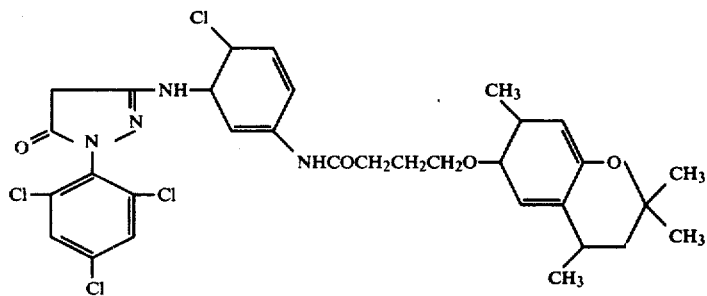 (M-9)
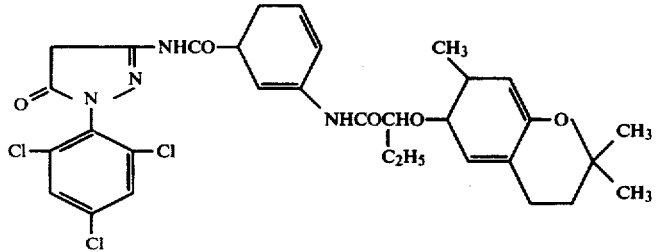 (M-10)
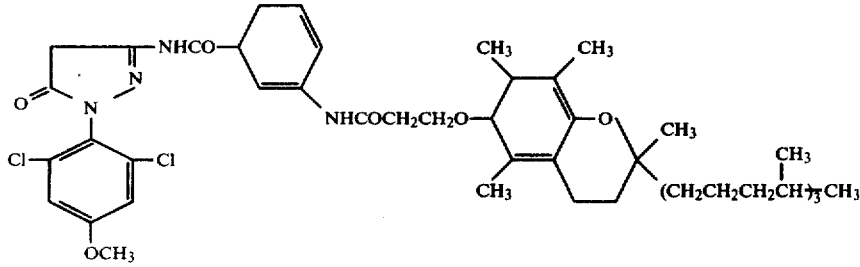 (M-11)
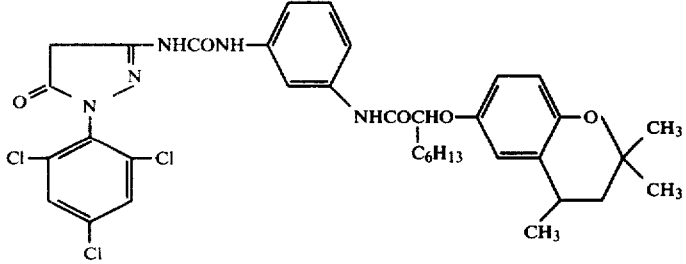 (M-12)

-continued
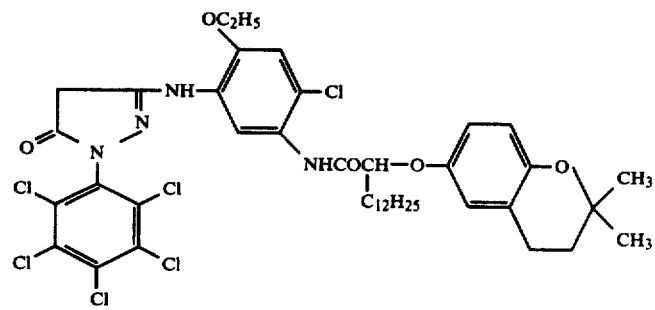
(M-13)
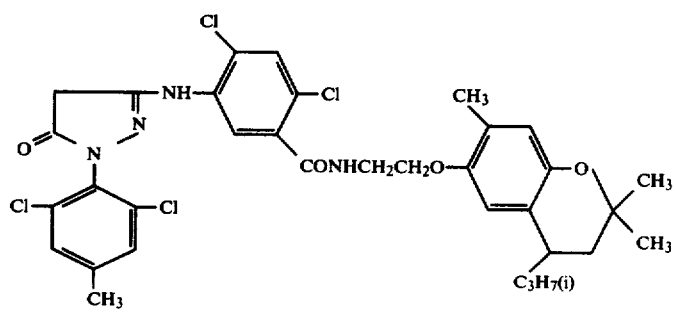
(M-14)
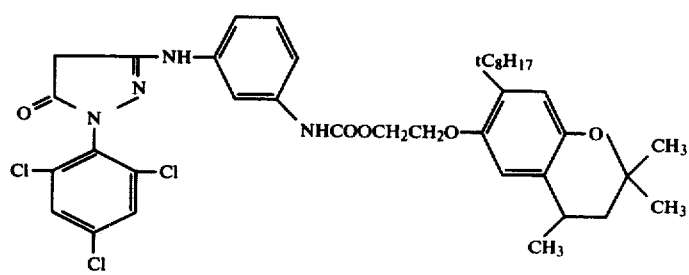
(M-15)
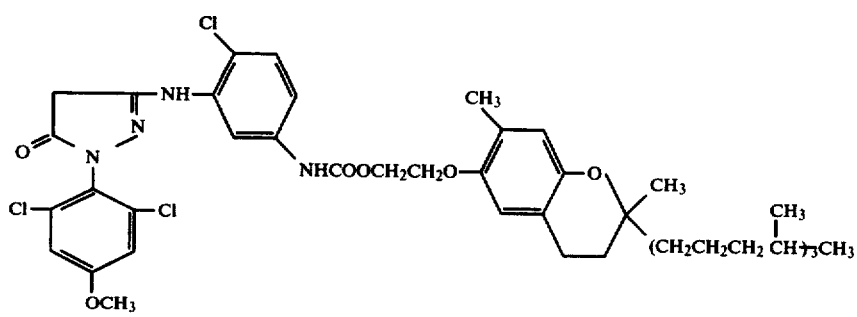
(M-16)
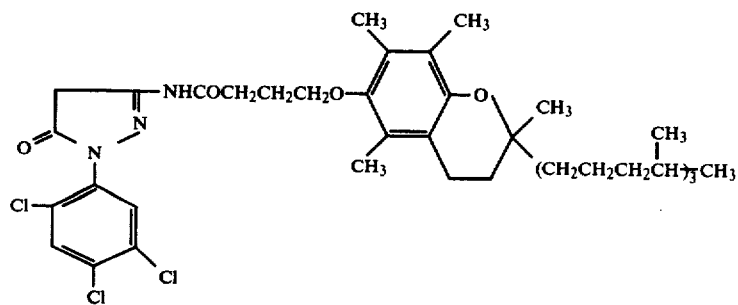
(M-17)

-continued
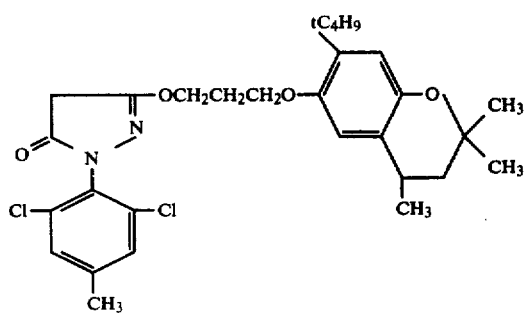 (M-18)
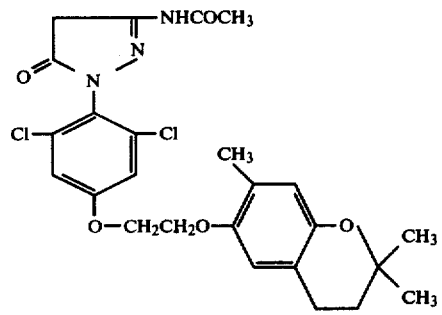 (M-19)
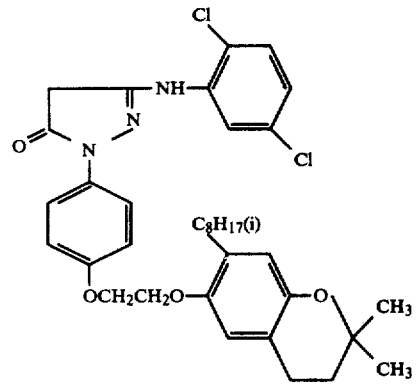 (M-20)
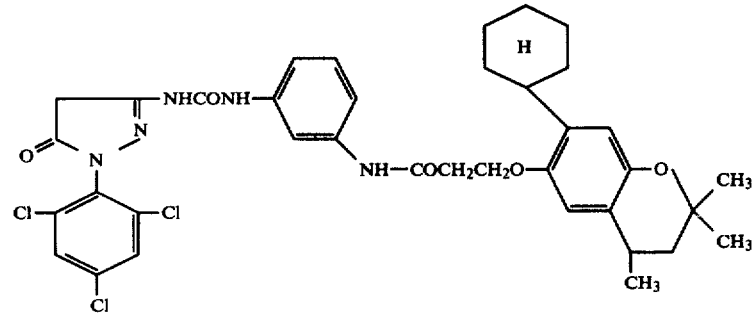 (M-21)
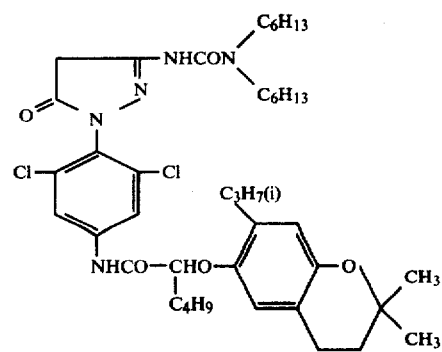 (M-22)

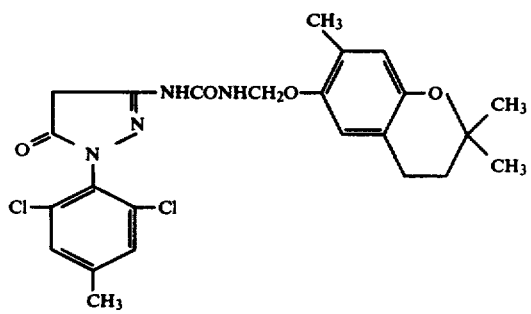
(M-23)
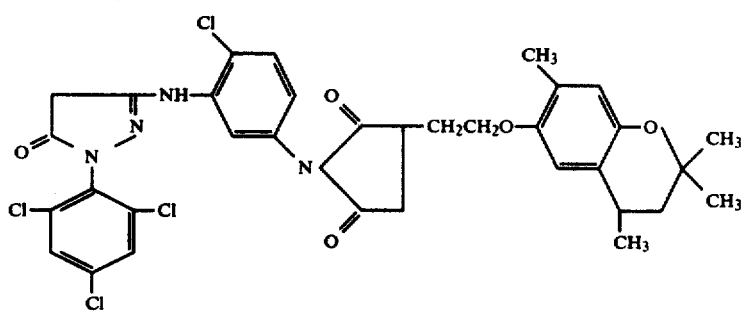
(M-24)
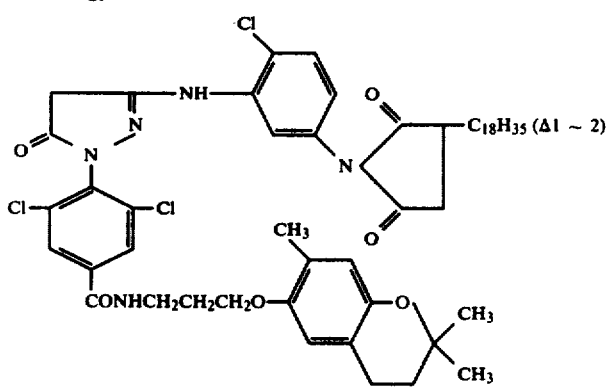
(M-25)
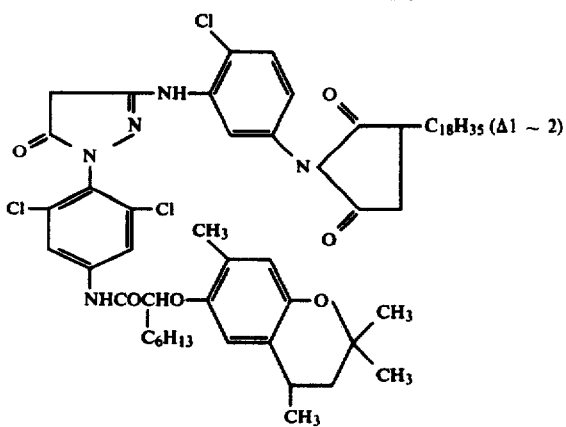
(M-26)
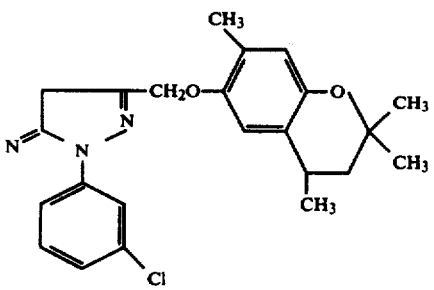
(M-27)

-continued
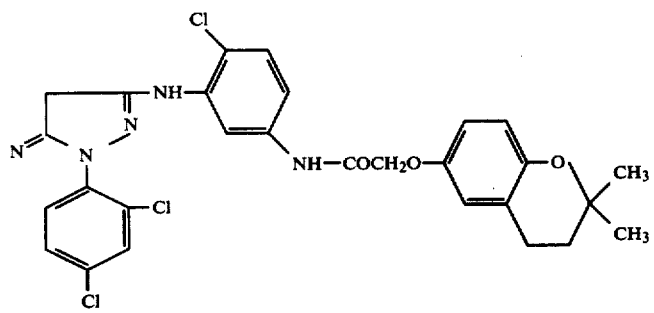 (M-28)
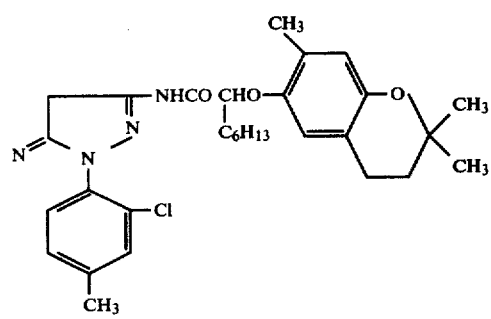 (M-29)
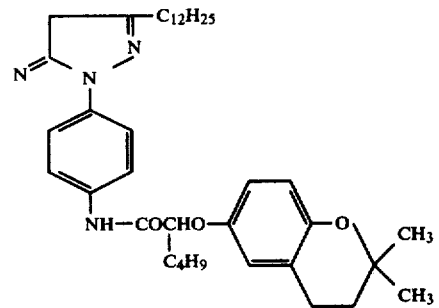 (M-30)
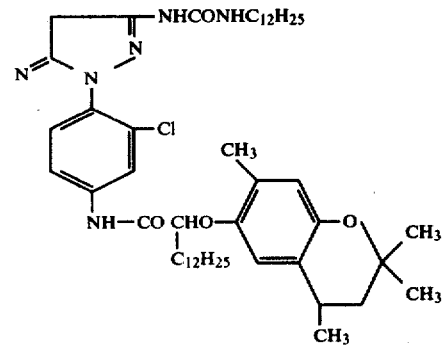 (M-31)
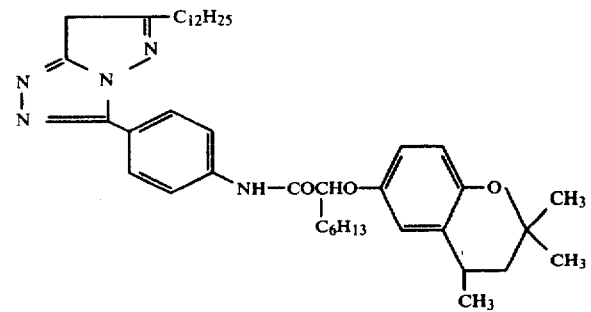 (M-32)

-continued
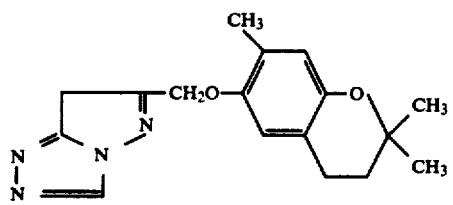 (M-33)
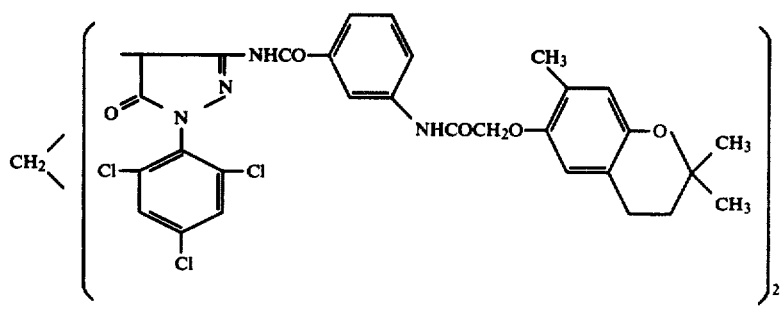 (M-34)
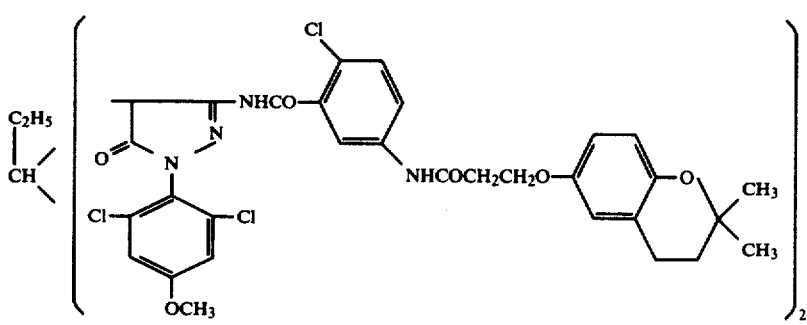 (M-35)
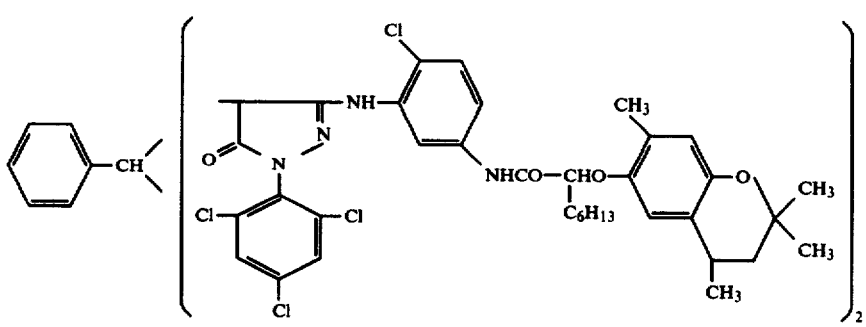 (M-36)
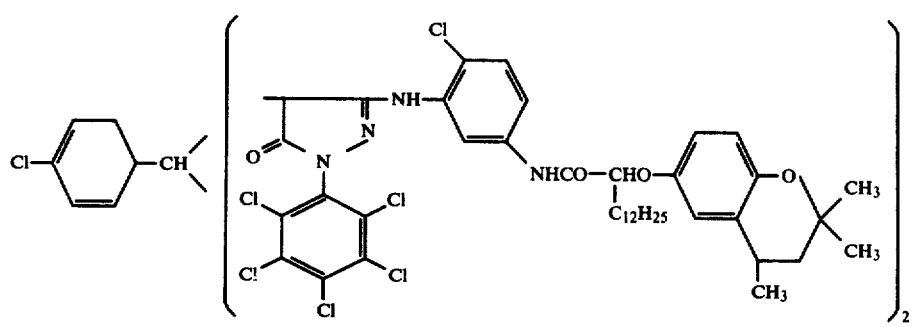 (M-37)

-continued
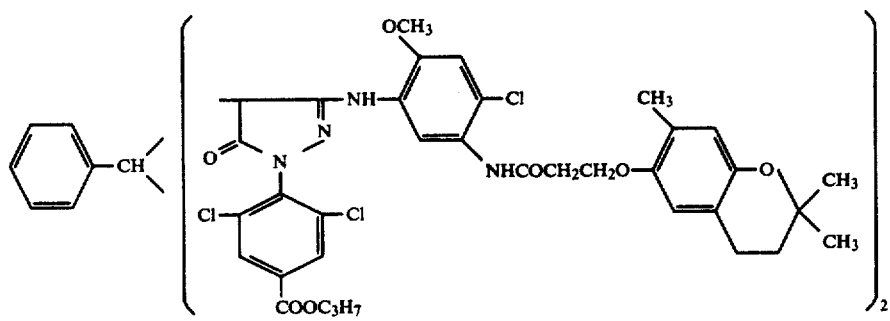
(M-38)
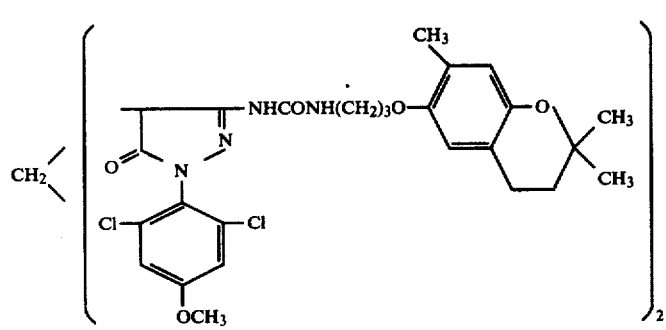
(M-39)
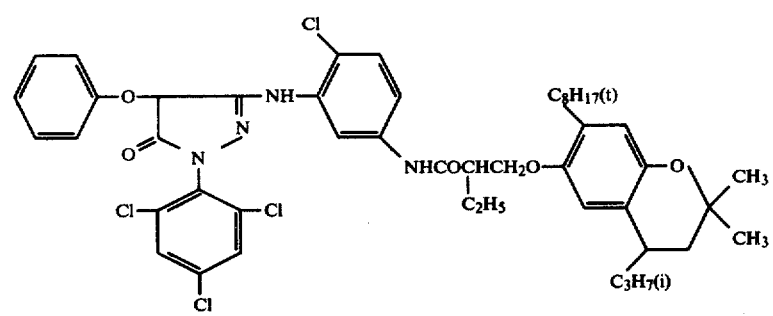
(M-40)
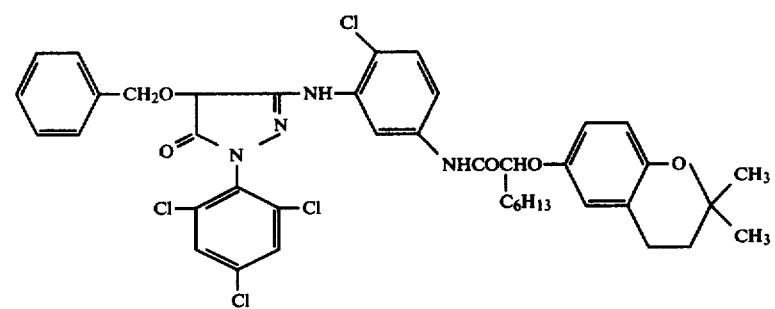
(M-41)
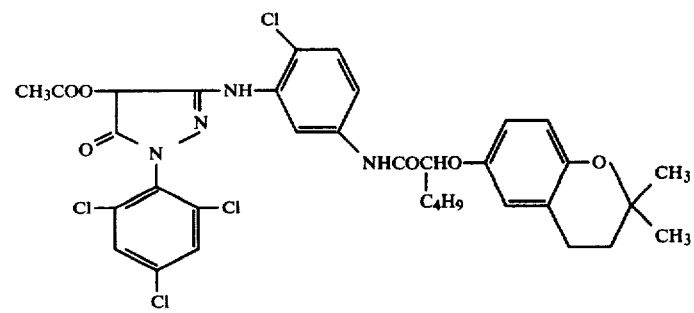
(M-42)

-continued
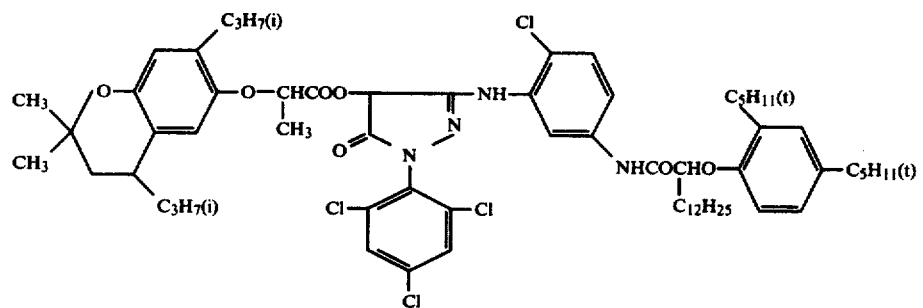 (M-43)
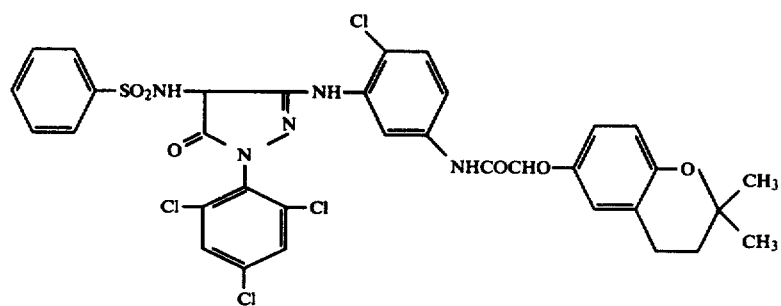 (M-44)
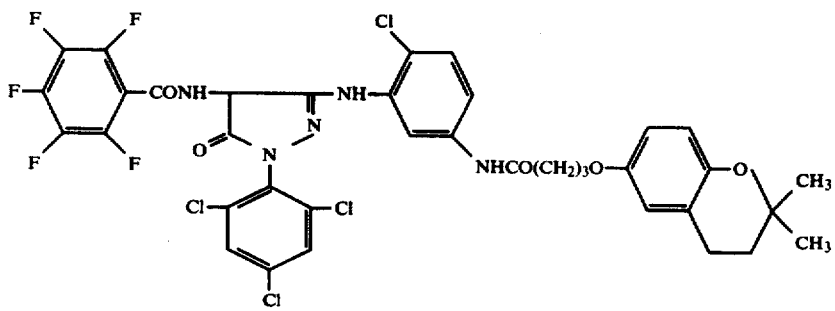 (M-45)
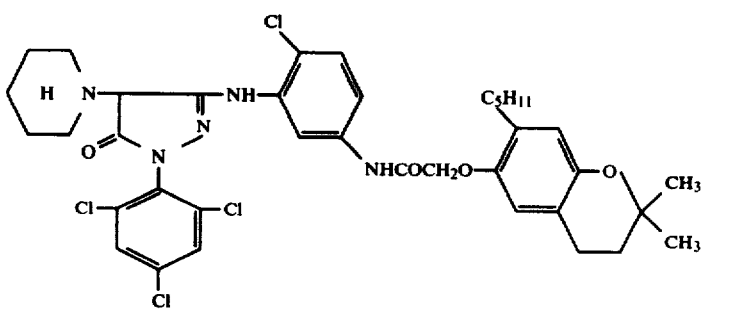 (M-46)
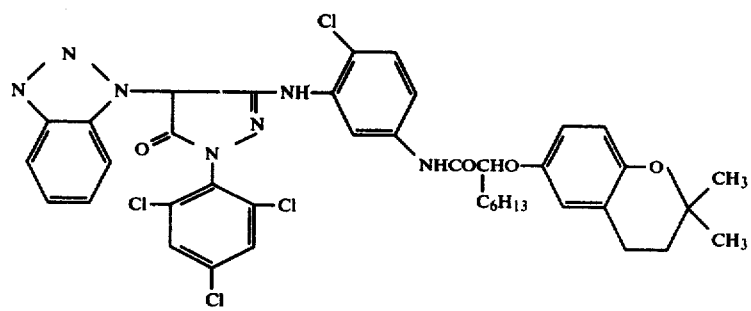 (M-47)

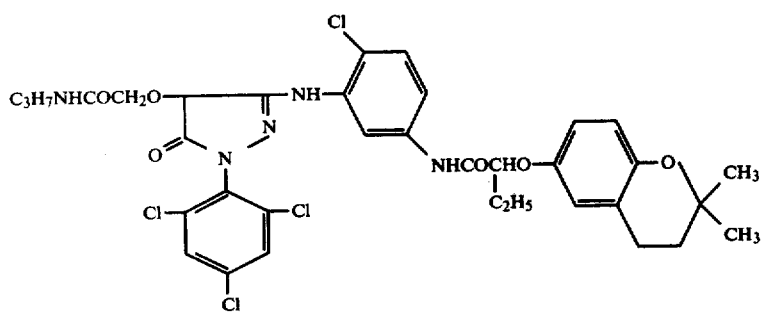
(M-48)
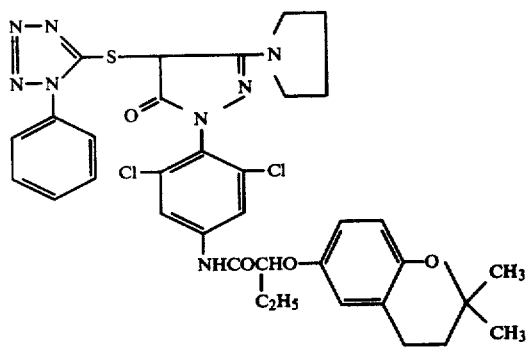
(M-49)
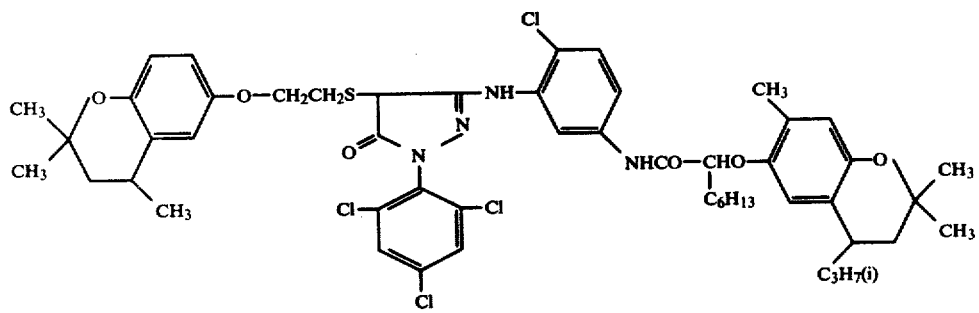
(M-50)
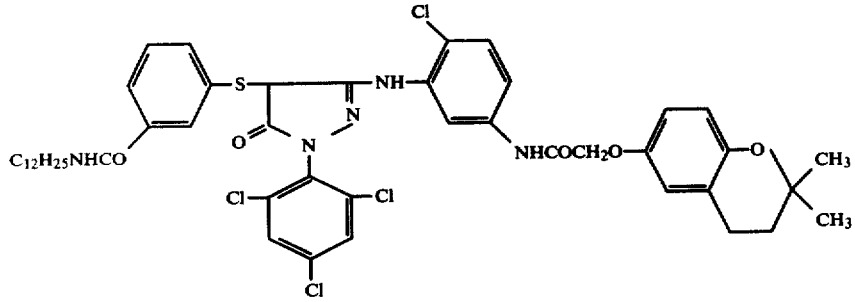
(M-51)
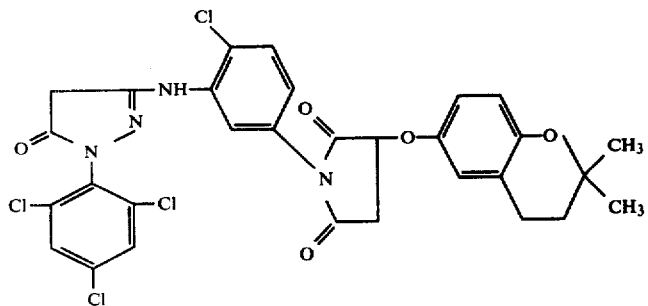
(M-52)

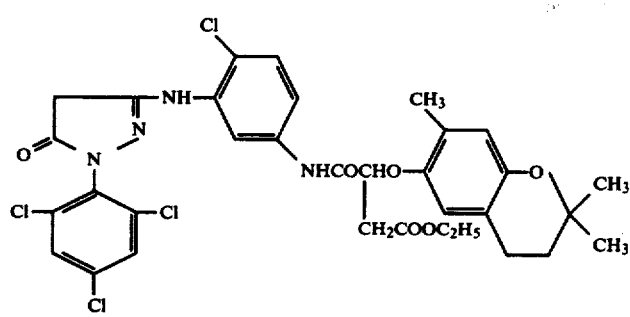
(M-53)
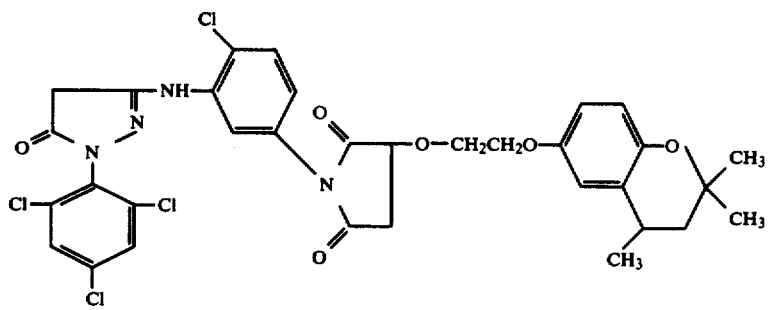
(M-54)
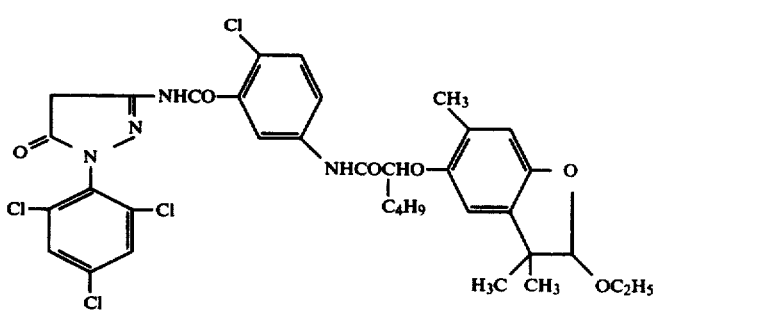
(M-55)
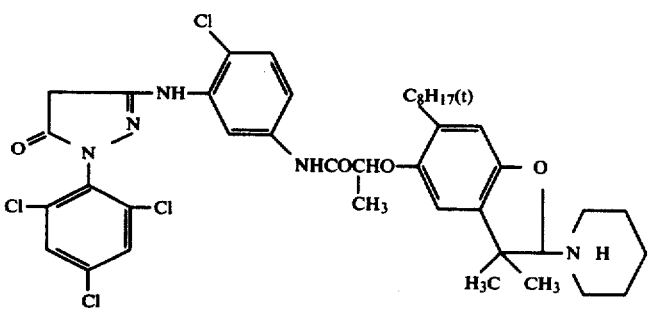
(M-56)
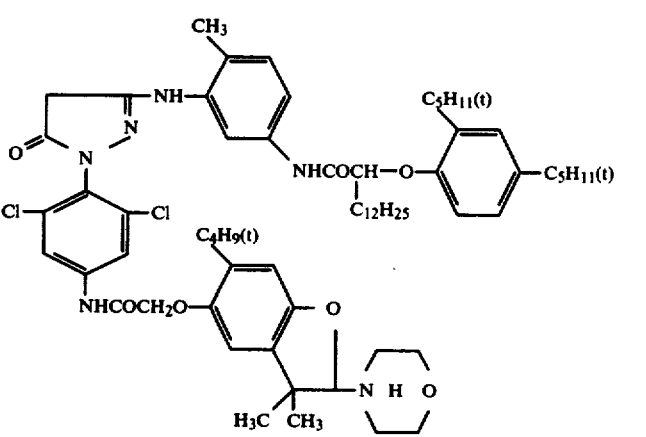
(M-57)

-continued
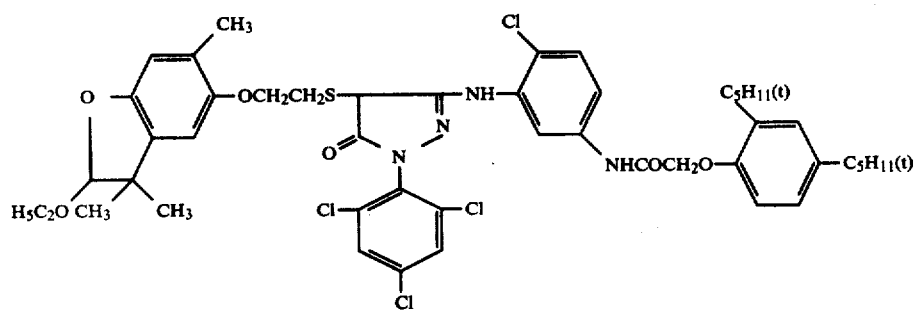 (M-58)
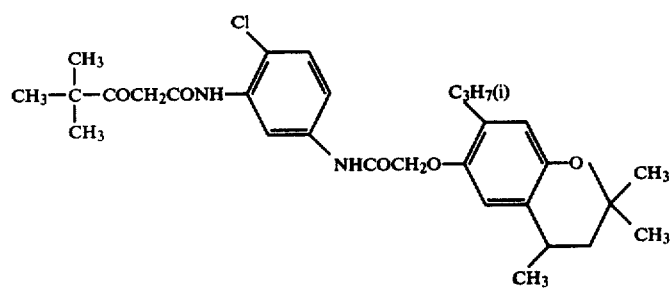 (Y-1)
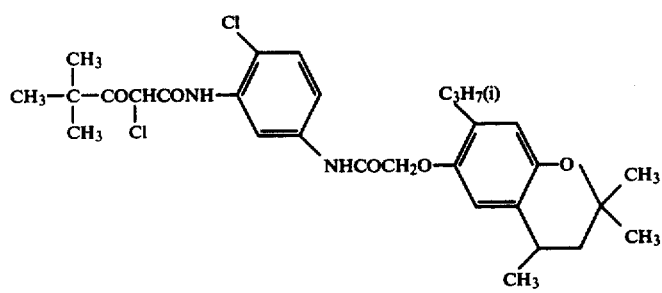 (Y-2)
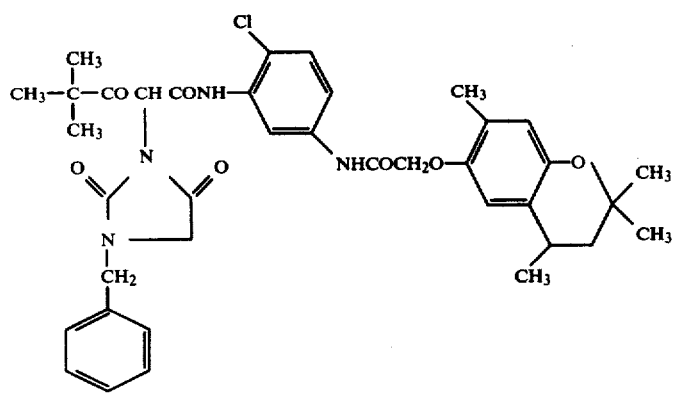 (Y-3)
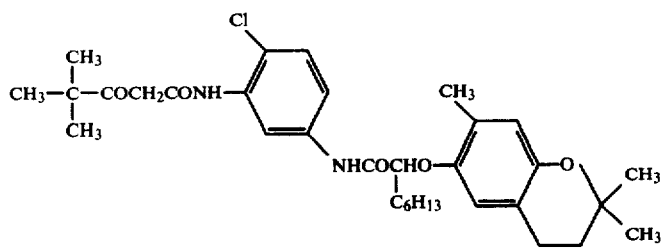 (Y-4)

-continued
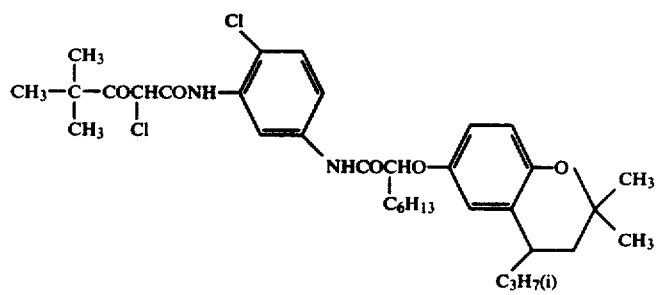 (Y-5)
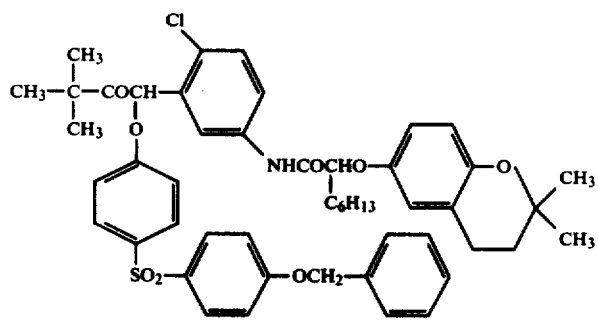 (Y-6)
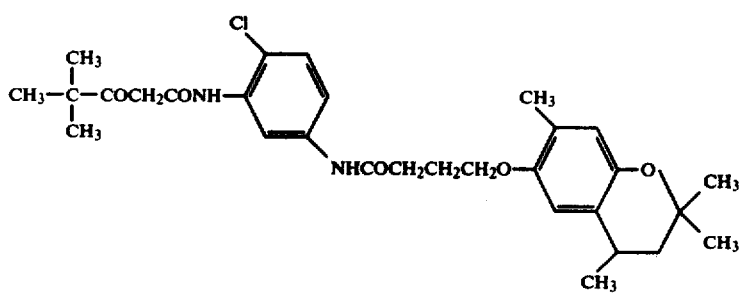 (Y-7)
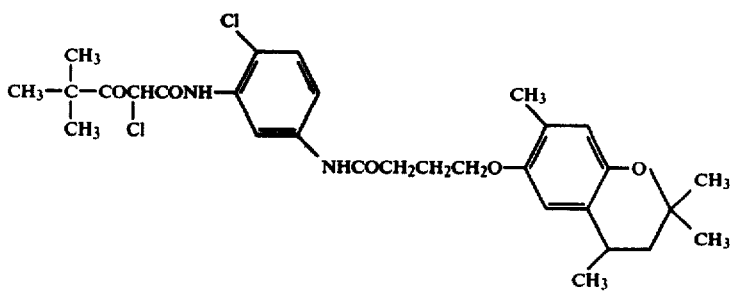 (Y-8)
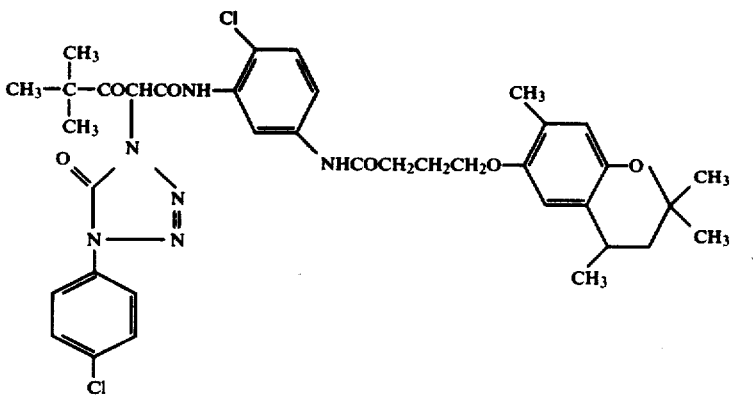 (Y-9)

-continued
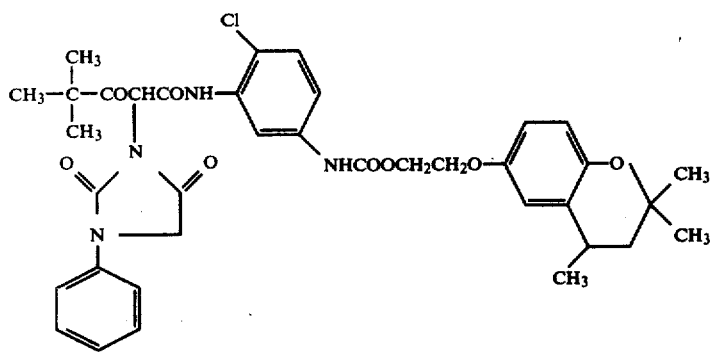 (Y-10)
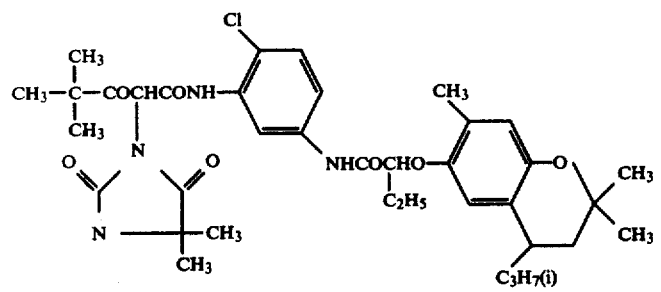 (Y-11)
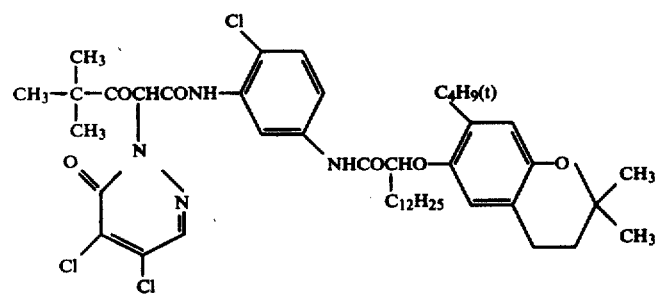 (Y-12)
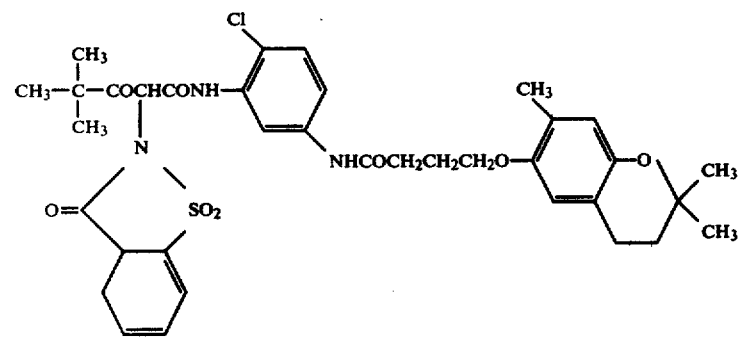 (Y-13)
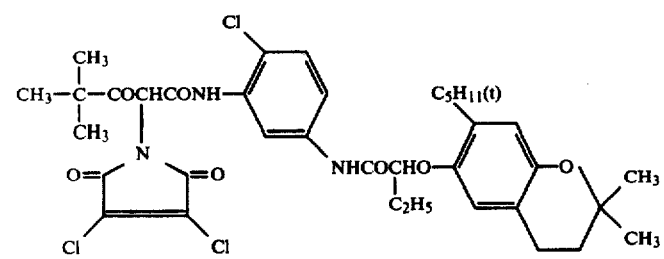 (Y-14)

-continued
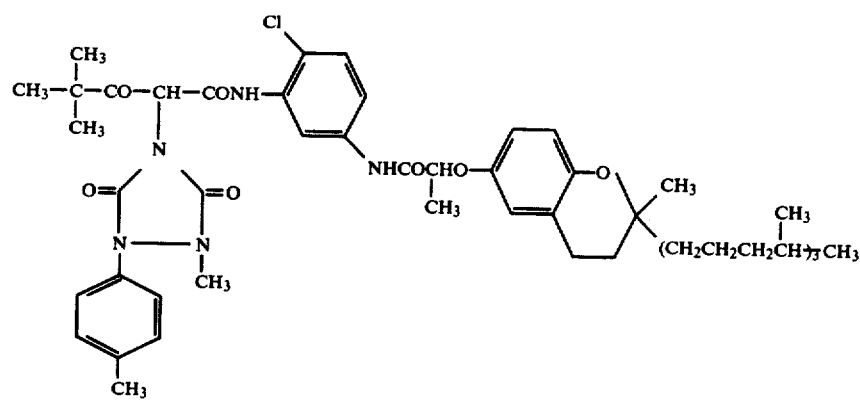
(Y-15)
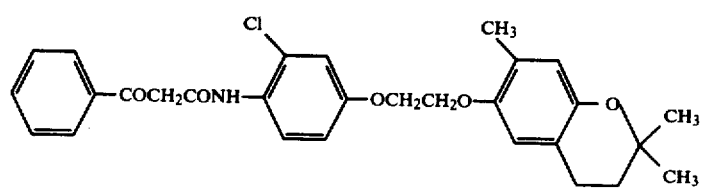
(Y-16)
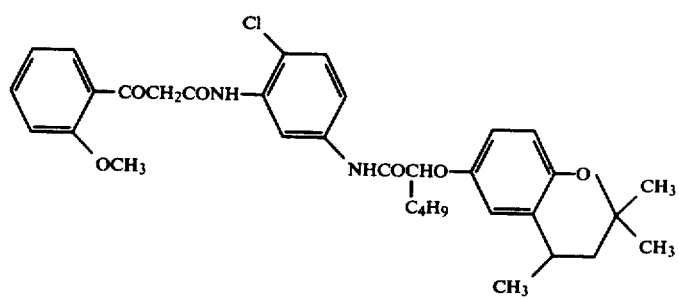
(Y-17)
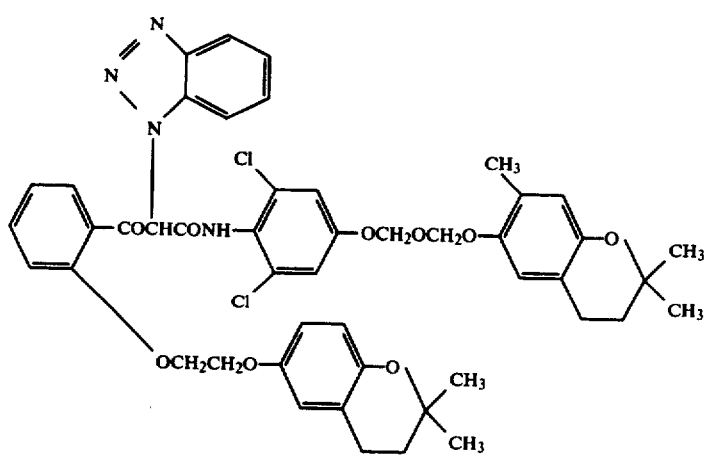
(Y-18)
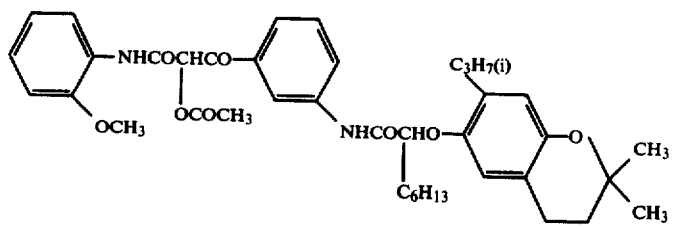
(Y-19)

-continued
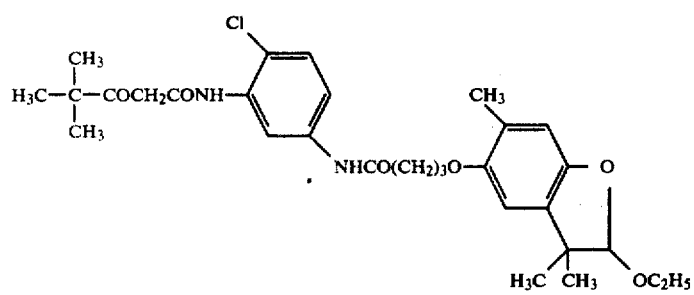
(Y-20)
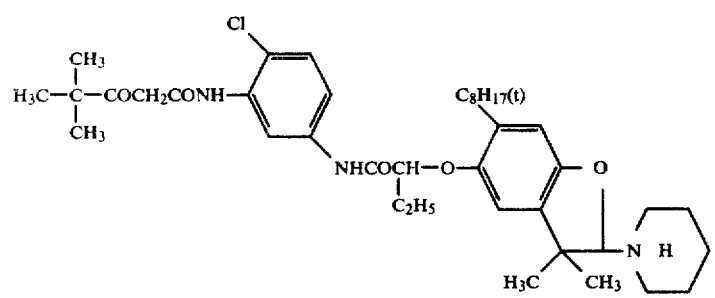
(Y-21)
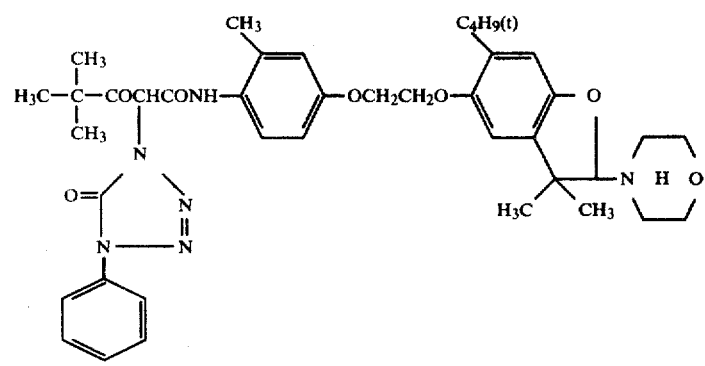
(Y-22)
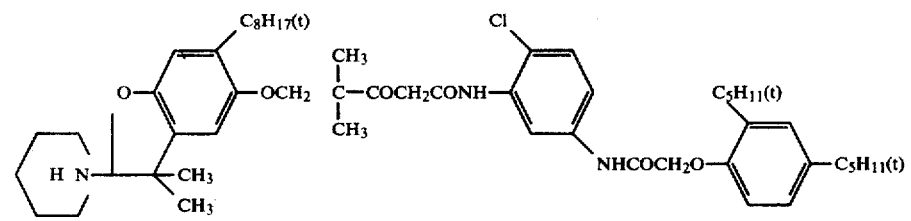
(Y-23)
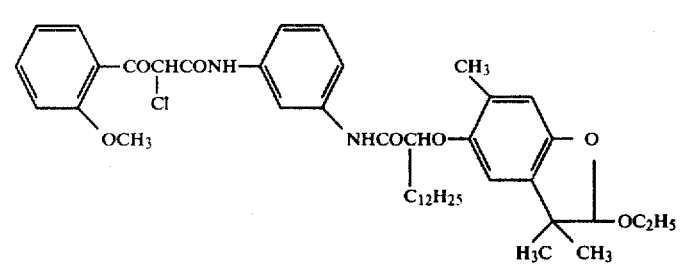
(Y-24)

-continued

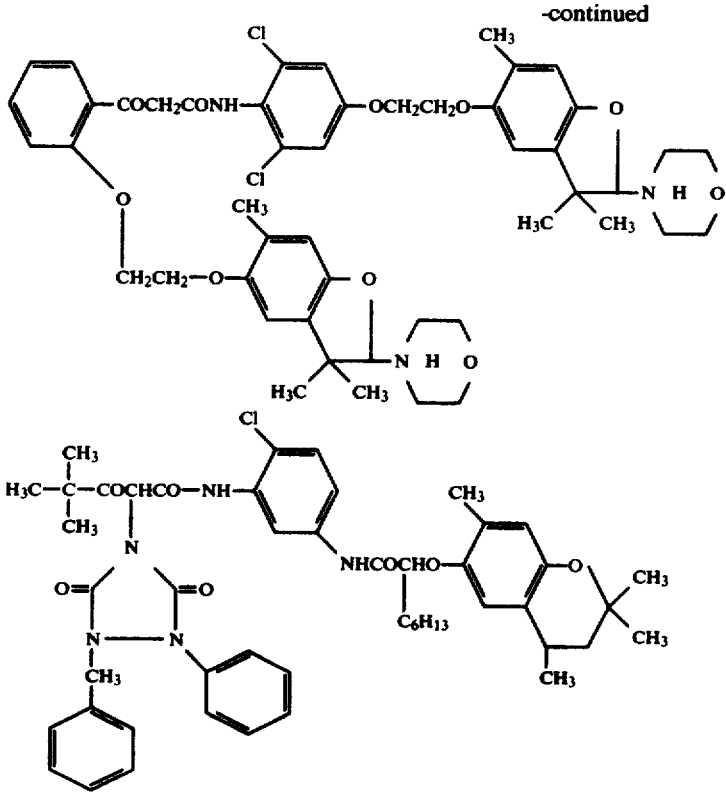

(Y-25)

(Y-26)

The couplers of the present invention can be synthesized, according to the procedures disclosed, for example, in U.S. Pat. Nos. 2,275,292, 2,428,054, 2,600,788, 2,908,573, 3,152,896, 3,253,294, 3,277,155 and 3,311,476, by converting a 6-hydroxychroman or couamaran compound into a desired ether derivative or ester derivative and subjecting said derivative to condensation reaction with a couplers intermediate used in the usual synthesis of couplers, or alternatively by subjecting said derivative used as a starting compound to the usual procedure employed in coupler synthesis.

Typical examples of the synthesis of couplers of the present invention are illustrated hereinafter.

SYNTHESIS EXAMPLE 1

Preparation of Exemplified coupler (M-4)

(a) Synthesis of intermediate compound (1) [α-(2,2,4,7-tetramethyl-6-chromanoxy)-hexanoic acid ester]

A solution of 6.9 g. (0.3 mole) of metallic sodium in 250 ml of absolute methanol is charged with 41.2 g. (0.2 mole) of 2,2,4,7-tetramethyl-6-chromanol and allowed to undergo reaction for 30 minutes by heating under reflux. After the reaction, the ethanol is distilled off under reduced pressure, and the resulting crystals are suspended in 120 ml of xylene. The suspension is charged with 49 g. (0.22 mole) of ethyl α-bromo-n-hexanoate and allowed to undergo reaction for 3 hours by heating under reflux. The reaction liquid is poured into 1.2 liters of water and then extracted with n-hexane, followed by water-washing. Thereafter, the extract is washed with a cold aqueous sodium hydroxide solution, washed with water and then dried over sodium sulfate. Concentration under reduced pressure followed by vacuum distillation gives 41.8 g. (60% yield) of a colorless viscous liquid as a fraction of b.p. 140°–145° C./0.017 mm Hg.

(b) Synthesis of intermediate compound (2) [α-(2,2',4,7-tetramethyl-6-chromanoxy)-hexanoic acid]

A solution of 34.8 g. (0.1 mole) in 120 ml of ethanol is charged with 20 ml of an aqueous solution of 12 g. (0.3 mole) of sodium hydroxide and allowed to undergo hydrolysis for 1 hour by heating under reflux. About ¼ of the ethanol is distilled off under reduced pressure, and the residue is poured into 400 ml of ice-cooled water containing 38 ml of concentrated hydrochloric acid, extracted with ethyl acetate, washed with water and then dried over sodium sulfate. Concentration under reduced pressure gives 31 g. (98% yield) of a pale brown viscous liquid. The compound thus obtained is used, as is, in the subsequent reaction.

(c) Synthesis of Exemplified coupler (M-4)

A solution of 16 g. (0.05 mole) of the intermediate compound (2) in 150 ml of carbon tetrachloride is charged with 11.5 g. (0.055 mole) of phosphorus pentachloride and is allowed to undergo reaction for 1 hour by heating under reflux. After generation of hydrochloric acid ceases, the resulting phosphorus oxychloride and the solvent are distilled off under reduced pressure to obtain oily products. A solution of the oily product in 150 ml of acetonitrile is charged with 14 g. (0.035 mole) of 1-(2,4,6-trichlorophenyl)-3-(5-amino-2-chloroanilino)-5-pyrazolone and 5 g. of pyridine and allowed to undergo reaction for 1 hour by heating under reflux. After the reaction, the reaction liquid is treated with active carbon, filtered and then concentrated under reduced pressure to obtain a pale brown powder. The powder is recrystallized from a mixture of n-hexane and chloroform to obtain 21.5 g. (61% yield) of white crystals, m.p. 110°–114° C. According to nuclear magnetic resonance spectrum (NMR), infrared spectrum (IR), mass spectrum (MS) and elementary analysis, it has been confirmed that the white crystalline product is the title end product.

Elementary analysis for $C_{34}H_{36}Cl_4N_4O_4$. Calculated (%): C: 57.79; H: 5.10; N: 7.93; Cl: 20.11. Found: (%): C: 57.97; H: 5.23; N: 8.12; Cl: 20.30.

SYNTHESIS EXAMPLE 2

Preparation of Exemplified Coupler (M-5)

(a) Synthesis of intermediate compound {ethyl-[α(2,2,4,7-tetramethyl-6-chromanoxy)-octanoate]}

In a solution of 87.5 g. of metallic sodium in 3 liters of absolute ethanol is dissolved 515 g of 2,2,4,7-tetramethyl-6-chromanol, and the resulting solution is heated under reflux. After 30 minutes, the solvent is distilled off under reduced pressure to obtain crystals, and the residue is suspended in 5 liters of anhydrous xylene and charged with 750 g. of ethyl α-bromooctanoate. The suspension is allowed to undergo reaction with stirring for 3.5 hours and reflux. After reaction, the reaction liquid is poured into 15 liters of ice-cold water and then extracted with n-hexane. After water-washing, the extract is washed with a cold 10% aqueous sodium hydroxide solution, followed by water-washing, and then dried over sodium sulfate. The solvent is distilled off, and the residue is vacuum distilled to obtain 685 g. (73% yield) of a fraction having a boiling point 165° C./0.03 mm Hg.

(b) Synthesis of intermediate compound (2) {[α-(2,2,4,7-tetramethyl-6-chromanoxy)-octanoic acid]}

A solution of 565 g. of the intermediate compound (2) in 2.8 liters of ethanol is charged with a solution of 185 g. of sodium hydroxide in 285 ml of water and allowed to undergo reaction for 1 hour by heating on a hot water bath under reflux. After reaction, about ½ of the ethanol is distilled off and the remaining reaction liquid is poured with stirring into a mixed solution comprising 5.7 liters of ice-cold water and 570 ml of concentrated hydrochloric acid. An oily product which separates is extracted with ethyl acetate, washed with water and then dried over sodium sulfate. After drying, the ethyl acetate is distilled off to obtain the title compound in a syrup form as a fraction having a b.p. of 194°–196° C./0.1 mm Hg. The compound thus obtained is sufficiently usable in the subsequent step even without being subjected to distillation. The yield is 490 g. (93.5% yield).

(c) Synthesis of Exemplified coupler (M-5)

A solution of 45 g. of the intermediate compound (2) in 250 ml of carbon tetrachloride is charged with 30 g. of phosphorus pentachloride and allowed to undergo reaction for 1 hour by heating on a hot water bath with stirring under reflux. After reaction, the carbon tetrachloride and the resulting phosphorus oxychloride are completely distilled off. The resulting residue is dissolved in 500 ml of anhydrous acetonitrile, and the resulting solution is charged with 42.5 g. of 1-(2,4,6-trichlorophenyl)-3-(5-amino-2-chloro)-anilino-5-pyrazolone and then with 9.3 g. of pyridine and allowed to undergo reaction 1.5 hours by heating under reflux. After reaction, the reaction liquid is charged with 500 ml of water and extracted with ethyl acetate. The extract is washed with water and dried over sodium sulfate, and the solvent is then distilled off to obtain a syrup-like product. The syrup-like product is purified by means of column chromatography to obtain the title end product in a syrup form. The yield is 57.9 g. (67.3% yield). According to IR, NMR, MS and elementary analysis, it has been confirmed that the purified syrup-like product thus obtained is the title end product.

Elementary analysis for $(C_{36}H_{40}Cl_4N_4O_4)$. Calculated (%): C: 58.86; H: 5.45; N: 7.63; Cl: 19.35. Found (%): C: 58.98; H: 5.41; N: 7.70; Cl: 19.22.

SYNTHESIS EXAMPLE 3

Preparation of Exemplified coupler (M-7)

(a) Synthesis of intermediate compound (1) {ethyl[α-(2,2-dimethyl-6-chromanoxy)-tetradecanoate]}

In a solution of 55.2 g. of metallic sodium in 3 liters of absolute ethanol is dissolved 356 g. of 2,2-dimethyl-6-chromanol, and the resulting solution is heated for 30 minutes under reflux. Thereafter, the ethanol is distilled off under reduced pressure, and the resulting cyrstals are suspended in 5 liters of xylene. The suspension is charged with 737 g. of ethyl α-bromotetradecanoate and allowed to undergo reaction for 4 hours by heating with stirring under reflux. After reaction, the reaction liquid is poured into 15 liters of ice-cold water and then extracted with n-hexane. The resulting n-hexane layer is washed with water and then with a cold 10% aqueous sodium hydroxide solution to remove unaltered chromanol. The n-hexane layer is then further washed with water and dried over sodium sulfate. After drying, the solvent is distilled off, and the residue is vacuum distilled to obtain 675 g. (78.2% yield) of a fraction having a b.p. of 165°–169° C./0.002 mm Hg.

(b) Synthesis of intermediate compound (2) {[α-(2,2-dimethyl-6-chromanoxy)-tetradecanoic acid]}

A solution of 650 g. of the intermediate (1) compound in 3 liters of ethanol is charged with a solution of 185 g. of sodium hydroxide in 285 ml of water and allowed to undergo reaction on a hot water bath under reflux. After 1 hour, about ½ of the ethanol is distilled off and the residue is poured with stirring into a mixed solution comprising 5.7 liters of ice-cold water and 570 ml of concentrated hydrochloric acid, whereby an oily product separates. The oily products-containing liquid is extracted with ethyl acetate, and the ethyl acetate layer is collected, washed with water and then dried over sodium sulfate.

After drying, the ethyl acetate is distilled off to obtain 396 g. (98% yield) of the title compound in a syrup state. The compound thus obtained can be used without purification in the subsequent reaction.

(c) Synthesis of Exemplified coupler (M-7)

A solution of 20.2 g. of the intermediate compound (2) in 120 ml of carbon tetrachloride is charged with 11.5 g. of phosphorus pentachloride and allowed to undergo reaction on a hot water bath with thorough stirring under reflux. After 1 hour, the carbon tetrachloride and the resulting phosphorus oxychloride are completely distilled off. The resulting syrup-like residue is dissolved in 300 ml of anhydrous acetonitrile, and the solution is charged with 18.2 g. of 1-(2,4,6-trichlorophenyl)-3-(5-amino-2-chloro)-anilino-5-pyrazolone and allowed to undergo reaction by heating with thorough stirring under reflux. After 6 hours, the reaction mother liquor after filtration is poured into 300 ml of ice-cold water and then extracted with ethyl acetate. The ethyl acetate layer is washed with water and dried over sodium sulfate and then the solvent is distilled off to obtain a syrup-like product which is then purified by means of silica gel column chromatography using a 95:5 mixture of benzene and acetone as a developing solvent to obtain 43.5 g. (55.1% yield) of a syrup-like product. According to IR, NMR, MS and elementary analysis, it has been confirmed that the syrup-like product thus obtained is the title end compound.

Elementary analysis ($C_{40}H_{48}Cl_4N_4O_4$). Calculated (%): C: 60.76; H: 6.08;N: 7.09; Cl: 17.98. Found: (%): C: 60.82; H: 6.14; N: 6.95; Cl: 17.88.

SYNTHESIS EXAMPLE 4

Preparation of Exemplified coupler (M-9)

(a) Synthesis of intermediate compound (1) [α-(2,2,4,7-tetramethyl-6-chromanoxy)butyronitrile]

In a solution of 5 g. (2.2 moles) of metallic sodium in 300 ml of absolute ethanol is dissolved 30 g. (1.4 moles) of 2,2,4,7-tetramethylchromanol. The resulting solution is charged with 26 g. (1.62 mole) of γ-bromobutyronitrile and allowed to undergo reaction for 5 hours by heating under reflux. After separating the resulting salt by filtration, the filtrate is concentrated, and the residue is dissolved in benzene. The solution is washed with an aqueous alkaline solution and then with water, dried over sodium sulfate and then concentrated under reduced pressure. The resulting solid residue is recrystallized from 500 ml of ethanol to obtain 26 g. (60% yield) of colorless needles, m.p. 74°-75° C.

(b) Synthesis of intermediate compound (2) [α-(2,2,4,7-tetramethyl-6-chromanoxy)butanoic acid]

A solution of 26 g. of the intermediate compound (1) in 500 ml of hot ethanol is charged with 400 ml of an aqueous solution of 18 g. of potassium hydroxide and allowed to undergo hydrolysis for 8 hours by heating under reflux. After concentrating the ethanol under reduced pressure, the residual aqueous solution is acidified with hydrochloric acid, extracted with ethyl acetate, washed with water, dried over sodium sulfate and then concentrated under reduced pressure to obtain a white solid. Recrystallization from n-hexane gives 22 g. (75.3% yield) of prisms, m.p. 95°-97° C.

(c) Synthesis of Exemplified coupler (M-9)

A solution of 100 g. of the intermediate compound (2) in 1.3 liters of carbon tetrachloride is charged with 78 g. of phosphorus pentachloride and heated with stirring under reflux. After 1 hour, the carbon tetrachloride and the resulting phosphorus oxychloride are completely distilled off under reduced pressure. The residue is dissolved in 1.5 liters of acetonitrile, and the solution is charged with 124 g. of 1-(2,4,6-trichlorophenyl)-3-(5-amino-2-chloro)-anilino-5-pyrazolone and heated with stirring under reflux. After 6 hours, the reaction mixture is filtered and the mother liquor is poured into 3 liters of ice-cold water to obtain crystals. After drying, the crystals are recrystallized from benzene to obtain 179 g. (77.2% yield) of the title end product, m.p. 125° C. According to NMR, IR, MS and elementary analysis, it has been confirmed that the end product thus obtained is the title compound.

Elementary analysis ($C_{32}H_{32}Cl_4N_4O_4$). Calculated (%): C: 56.64; H: 4.72; N: 8.26; Cl: 20.94. Found (%): C: 56.39; H: 4.91; N: 8.07; Cl: 21.05.

SYNTHESIS EXAMPLE 5

Preparation of Exemplified coupler (Y-7)

(a) Synthesis of intermediate compound (1) {2-chloro-5-[α-(2,2,4,7-tetramethylchloromanoxy)butyramido]nitrobenzene}

A solution of 22 g of the intermediate compound (2) of Synthesis Example 4 in 200 ml of carbon tetrachloride is charged with 17.5 g. of phosphorus pentachloride and refluxed for 1 hour. After generation of hydrochloric acid ceases, the resulting phosphorus oxychloride and the solvent are distilled off under reduced pressure to obtain a viscous acid chloride.

The acid chloride is dissolved in 70 ml of acetone, and the solution is added dropwise to a solution of 12.5 g. of 4-chloro-3-nitroaniline and 7 g of pyridine in 70 ml of acetone. Thereafter, the resulting solution is heated for 1 hour under reflux. After reaction, the reaction liquid is concentrated under reduced pressure to obtain a yellow viscous liquid. The liquid thus obtained is used in the subsequent reaction without subjecting the same to purification.

(b) Synthesis of intermediate compound (2) {2-chloro-5-[α-(2,2,4,7-tetramethyl-6-chromanoxy)-butyramido]anilide}

A solution of the intermediate compound (1) in 140 ml of ethanol is charged with 30 g. of zinc powder and further charged gradually under reflux with 120 ml of a 80% aqueous acetic acid solution, and the resulting solution is allowed to undergo reaction for 3 hours under reflux. After reaction, the reaction liquid is filtered and then concentrated under reduced pressure. The residue is stirred with hot benzene, and the benzene layer is washed several times with an aqueous hydrochloric acid solution and water, dried over sodium sulfate and then concentrated under reduced pressure to obtain a white powder. The white powder is recrystallized from a mixture of n-hexane and acetone to obtain 18 g. of colorless crystals, m.p. 114°-117° C.

(c) Synthesis of Exemplified coupler (Y-7)

A solution of 16.7 g. of the intermediate compound (2) in 100 ml of xylene is charged with 14 g. of ethyl α-pivaloylacetate and 1 ml of pyridine and heated under reflux. Subsequently, the mixture is subjected to a distillation apparatus, and the ethanol which is formed under ordinary pressure and the xylene solvent are distilled off. The reaction mixture is further conducted at 150° C. for 3 hours. After distilling off an excess of ethyl α-pivaloylacetate under reduced pressure, the residue is recrystallized from n-hexane to obtain 16 g. of colorless powdery crystals. According to NMR, IR, MS and elementary analysis, it has been confirmed that the crystal thus obtained is the title end product.

Elementary analysis ($C_{30}H_{39}Cl\ N_2O_5$). Calculated (%): C: 66.36; H: 7.19; N: 5.16; Cl: 6.54. Found (%): C: 66.53; H: 7.30; N: 5.04; Cl: 6.60.

In accordance with the couplers of the present invention, not only is the light fastness of the dye image formed thereby particularly improved but also Y-stain which takes place in unexposed areas can be prevented by introducing the group represented by the aforementioned general formula [I] into any optional position in the molecule of the yellow coupler as well as of the magenta coupler.

It is known that generally indoaniline dyes formed from cyan couplers are structurally stable as compared with azomethine dyes. It is observed that light fastness is certainly improved when the group of the general formula [I] according to the present invention is introduced into the molecule of the indoaniline dye.

As an example of a coupler forming the indoaniline dye having introduced therein the group of the general formula I according to the present invention, there is disclosed a compound of the following structure disclosed in Research Disclosure, Vol. 148, p. 53 (1976).

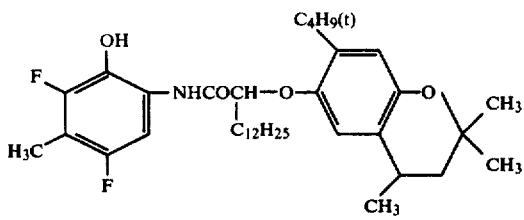

However, even when the group of the general formula [I] is introduced into cyan couplers, in general, which form indoaniline dyes as well as into the above-mentioned compound, the effect of improving light fastness thereby obtained is quite small and the effects of improving heat resistance and resistance to humidity are also small.

In contrast thereto, the couplers of the present invention have effects and advantages, which could not be anticipated from the conventional techniques namely, that the present couplers form azomethine dyes having markedly improved light fastness, which have excellent solubility in organic solvents and dispersibility in silver halide emulsions, which give dye images high in maximum color density and form dyes having their absorption wavelengths in the preferred ranges and, moreover, that the present couplers do not make opaque the photosensitive color materials containing the same and, at the same time, they are excellent not only in light fastness but also fastness to heat and humidity.

Generally, the couplers of the present invention are usually incorporated into silver halide emulsion layers of color photosensitive materials, but they may also be incorporated into any layers adjacent to the silver halide emulsion layer.

The couplers of the present invention are preferably incorporated, according to procedures disclosed in U.S. Pat. Nos. 2,322,027, 2,801,170, 2,801,171, 2,272,191 and 2,304,940, by dissolving them in high boiling solvents, if necessary, using low boiling solvents in combination therewith, and forming the resulting solutions into coupler dispersions. In that case, hydroquinone derivatives, ultraviolet absorbers, etc. may be freely usable, if necessary, in combination with such couplers, and the present couplers may also be usable in admixture of two or more. More particularly, one or two or more couplers of the present invention, if necessary, together with hydroquinone derivatives, ultraviolet absorbers, etc., are dissolved in such high boiling solvents as will be illustrated below, if necessary, using such low boiling solvents as will be mentioned hereinafter, the resulting solutions are mixed with an aqueous solution containing a hydrophilic binder such as gelatin and an anionic surface active agent such as alkylbenzenesulfonic acid or alkylnaphthalenesulfonic acid and/or a nonionic nonion type surface active agent such as sorbitan sesquioleate or sorbitan monolaurate, and the resulting mixture is subjected to a high speed rotary mixer, colloid mill or supersonic wave dispersion apparatus to obtain an emulsified dispersion which is then incorporated into silver halide emulsions. The high boiling solvents usable in the above case include, for example, organic acid amides, carbamates, esters, ketones, urea derivatives and the like, particularly di-n-butyl phthalate, tricresyl phosphate, triphenyl phosphate, di-isooctyl azelate, di-n-butyl sebacate, tri-n-hexyl phosphate, N,N-diethyl-caprylamide butyl, N,N-diethyl laurylamide, n-pentadecyl phenyl ether, di-octyl phthalate, n-nonylphenol, 3-pentadecyl ethyl ether, 2,5-di-secamylphenyl butyl ether, monophenyl-di-Q-chlorophenyl phosphate and fluorinated paraffin, and the low boiling solvents include, for example, methyl acetate, ethyl acetate, propyl acetate, butyl acetate, butyl propionate, cyclohexanol, diethylene glycol monoacetate, nitromethane, carbon tetrachloride, chloroform, cyclohexanetetrahydrofuran, methyl alcohol, acetonitrile, dimethylformamide, dioxane and methyl ethyl ketone (these high boiling and low boiling solvents may be used either singly or in admixture thereof).

Of the couplers of the present invention, those which are in a liquid state at ordinary temperature or which are relatively low in melting point may be also usable as solvents for oil-soluble coupler compounds in place of a part or whole of the aforementioned high boiling solvent.

The amount of the present coupler to be incorporated is not limited, but is preferably 10 to 100 g per mole of silver halide, and said amount may be suitably changed, if necessary.

Ultraviolet absorbers usable in combination with the couplers of the present invention include, for example, compounds of thiazolidone, benzotriazole, acrylonitrile and benzophenone types as disclosed in U.S. Pat. Nos. 2,739,888, 3,004,896, 3,253,921, 3,533,794, 3,692,525, 3,705,805, 3,738,837, 3,754,919, 3,052,636 and 3,707,375, and British Pat. No. 1,321,355. The use of these ultraviolet absorbers is of advantage to prevent the resulting dye images from fading due to actinic rays of shorter wavelength, and particularly the use, either singly or in combination, of Thinupin PS, 320, 326, 327 and 328 (products of Ciba-Geigy Co.) is of advantage.

Hydroquinone derivatives usable in combination with the couplers of the present invention include precursors thereof. By precursors as used herein are meant compounds which release hydroquinone derivatives on hydrolysis. Such precursors include, for example, such compounds in which one or two hydroxyl groups of the hydroquinone nucleus have been converted, for example, into

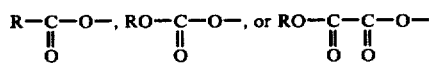

wherein R represents an aliphatic group such as alkyl or the like.

Representatives of the hydroquinone derivative used in the present invention include such compounds as represented by the following general formula [VIII].
General formula [VIII]

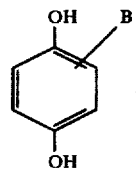

wherein B represents an alkyl group (e.g. methyl, t-butyl, t-amyl, octyl, t-octyl, dodecyl, octadecyl, etc.), an aryl group (e.g. phenyl, etc.), an alkoxy group (e.g. methoxy, butoxy, dodecyloxy, etc.), an aryloxy group (e.g. phenoxy, etc.), a carbamoyl group (e.g. methylcarbamoyl, dibutylcarbamoyl, octadecylcarbamoyl, phenylcarbamoyl, etc.), a sulfamoyl group (e.g. methylsulfamoyl, octadecylsulfamoyl, etc.), an acyl group (e.g. acetyl, octanoyl, lauroyl, etc.), an alkoxycarbonyl group (e.g. methoxycarbonyl, dodecyloxycarbonyl, etc.) or an aryloxycarbonyl group (e.g. phenyloxycarbonyl, etc.), and the alkyl moiety as well as the aryl moiety in the above-mentioned groups may include those substituted with such substituents as halogen, alkyl, aryl, alkoxy, aryloxy, carboxy, alkoxycarbonyl, aryloxycarbonyl, acyl, acyloxy, carbamoyl, sulfo, sulfamoyl, sulfonamido, N-alkylamino, N-arylamino, acylamino, imido or hydroxy group, and one to three out of the remaining three hydrogen atoms on an aromatic nucleus of the hydroquinone may be substituted by halogen atoms and one to three (may be the same or different) out of the groups defined as the B substituents.

Examples of the nucleically substituted hydroquinones used in the present invention are exemplified, for example, in U.S. Pat. Nos. 2,336,327, 2,360,290, 2,384,658, 2,403,721, 2,418,613, 2,675,314, 2,701,197, 2,704,713, 2,710,801, 2,722,556, 2,728,659, 2,732,300, 2,735,765, 2,816,028, 3,062,884 and 3,236,896, British Pat. Nos. 557,750 and 557,802, West German Patent Publication No. 2,149,789, Japanese Patent Publication No. 54116/1969, Japanese Laid-Open-to-Public Publication No. 2128/1971, and Journal of Organic Chemistry, Vol. 22, PP. 772–774.

Of the nucleically substituted hydroquinone derivatives, those which have carbon atoms contained in the substituents on the nucleus and amounting to 8 or more are low in diffusibility and suitable for being selectively made present in a specific hydrophilic layer of the photosensitive material.

Of the hydroquinone derivatives, those which have substituted or unsubstituted alkyl as the substituents on the nucleus are particularly useful.

Listed below are examples of the hydroquinone derivative used in the present invention, but those are to be construed as illustrative and not limitative.

| | |
|---|---|
| Hq - 1 | 2,5-di-tert-Octylhydroquinone |
| Hq - 2 | 2-tert-Octyl-5-methylhydroquinone |
| Hq - 3 | 2,6-di-n-Dodecyl-hydroquinone |
| Hq - 4 | 2-n-Dodecylhydroquinone |
| Hq - 5 | 2,2'-Methylenebis-5,5'-di-t-butylhydroquinone |
| Hq - 6 | 2,5-di-n-Octyl-hydroquinone |
| Hq - 7 | 2-Dodecylcarbamoylmethylhydroquinone |
| Hq - 8 | 2-(-n-Dodecyloxycarbonyl)ethyl-hydroquinone |
| Hq - 9 | 2-(N,N-Dibutylcarbamoyl)hydroquinone |
| Hq - 10 | 2-n-Dodecyl-5-chloro-hydroquinone |
| Hq - 11 | 2-(2-Octadecyl)-5-methylhydroquinone |
| Hq - 12 | 2,5-di-(p-Methoxyphenyl)hydroquinone |
| Hq - 13 | 2-tert-Octylhydroquinone |
| Hq - 14 | 2-{β-[3-(3-Sulfobenzamido)benzamido]}ethyl-hydroquinone |
| Hq - 15 | 2,5-Dichloro-3,6-diphenylhydroquinone |
| Hq - 16 | 2,6-Dimethyl-3-tert-octylhydroquinone |

-continued

| | |
|---|---|
| Hq - 17 | 2,3-Dimethyl-5-tert-octylhydroquinone |
| Hq - 18 | 2-{β-(Dodecanoyloxy)ethyl}carbamoylhydroquinone |
| Hq - 19 | 2-Dodecyloxycarbonylhydroquinone |
| Hq - 20 | 2-{β-(4-Octanamidophenyl)ethyl}hydroquinone |
| Hq - 21 | 2-Methyl-5-dodecylhydroquinone |

The above-listed hydroquinone derivatives are used either singly or in combination of two or more, and the amount of said derivative to be incorporated is usually preferably 0.01 to 10 moles, particularly preferably 0.1 to 3 moles, per mole of a coupler present in the coupler-containing color photosensitive material.

Silver halide emulsions used in the color photosensitive material according to the present invention are generally emulsions prepared by dispersing silver halide particles in a hydrophilic colloid. The silver halide includes silver chloride, silver bromide, silver iodide, silver chlorobromide, silver chloroiodobromide and the mixtures thereof. These silver halides are prepared by various procedures such as the ammonia process, neutral process, a so-called conversion process and simultaneous mixing process. The hydrophilic colloid, in which the silver halide is dispersed, includes gelatin and gelatin derivatives such as phthalated gelatin and malonated gelatin. In place of a part or whole of this gelatin and such gelatin derivatives, there may also be used albumin, agar, gum arabic, alginic acid, casein, partially hydrolyzed cellulose derivatives, polyvinyl alcohol, partially hydrolyzed polyvinyl acetate, polyacrylamide, imidated polyacrylamide, polyvinylpyrrolidone and copolymers of these vinyl compounds. Further, the silver halide emulsions may be subjected to chemical sensitization using various kinds of sensitizing dyes in order to impart sensitivity at a desired wavelength region. Preferable sensitizing dyes include cyanine dyes, merocyanine dyes or composite cyanine dyes, which may be used either singly or in combination, disclosed, for example, in U.S. Pat. Nos. 1,939,201, 2,072,908, 2,688,545, 2,739,149, 2,912,329, 2,213,995, 2,493,748, 2,519,001, 3,397,060 and 3,628,964, West German Pat. No. 1,242,588, British Pat. Nos. 1,195,302, 1,242,588, 1,293,862 and 505,979, West German Patent Publication Nos. 2,030,326 and 2,121,780, Japanese Patent Publication Nos. 4936/1968 and 14030/1969. If necessary, moreover, the emulsions may be used after being incorporated with various photographic additives which may be used either singly or in combination. These photographic additives include, for example, chemical sensitizing agents such as gold compounds, noble metal salts of platinum, palladium, iridium, rhodium, ruthenium and the like, sulfur compounds, reducing substances or thioether compounds, quaternary ammonium salt compounds or polyalkyleneoxide compounds, stabilizing agents such as triazoles, imidazoles, azaindenes, benzothiazolium compounds, zinc compounds, cadmium compounds and mercaptans, chromium salts, zirconium salts and mucochloric acid disclosed in U.S. Pat. Nos. 1,574,944, 2,399,083, 2,410,689, 2,448,060, 2,487,850, 2,518,698, 2,521,925, 2,521,926, 2,540,085, 2,540,086, 2,566,245, 2,566,263, 2,597,856, 2,597,915, 2,598,079, 2,983,610, 3,189,458, 3,201,254 and 3,501,313; film hardening agents including those of aldehyde type, triazine type, polyepoxy compounds, active halogen compounds, ketone compounds, acryloyl type, triethylenephosphamide type and of ethyleneimine type; plasticizers such as glycerin and 1,5-pentanediol: fluorescent brightening agents; antistatic agents and coating aids disclosed in Japanese Patent Publication Nos. 7133/1959 and 1872/1971, British Pat. Nos. 686,440, 974,732, 994,869 and 1,332,647, U.S. Pat. Nos. 682,641, 2,725,295, 2,732,303, 2,732,316, 2,983,611, 3,017,280, 3,091,537, 3,100,704, 3,103,437, 3,321,313, 3,325,287, 3,362,827, 3,543,292, 3,635,718 and 3,736,320. The emulsion prepared in the manner explained above is incorporated with a dispersion prepared by dispersing therein the couplers, etc. according to the present invention as aforesaid and then coated on a support a as a film of such synthetic material such as cellulose acetate, cellulose nitrate, polycarbonate, polyethylene terephthalate or polystyrene, baryta paper, polyethylene-coated paper or glass plate, if necessary through a sub layer, antihalation layer, intermediate layer, yellow filter layer and protective layer provided on the support, whereby to obtain a color photosensitive material. The color photosensitive material according to the present invention may comprise therein not only one layer of a silver halide emulsion layer but also two or more layers of silver halide emulsion layers, and may also comprise two or more emulsion layers which are sensitive at the same wavelength region.

The color photosensitive material according to the present invention is a coupler-containing internal type color photosensitive material and, after exposure, is advantageously color developed according to the color development method. The present color photosensitive material may be usable as a color photosensitive material in which both couplers and a color developing agent are present in the same one layer and are individually protected so that they may not be brought into contact with each other before exposure but may be brought into contact with each other after exposure, or as a color photosensitive material in which a color developing agent is present in a layer containing no couplers and said color developing agent is allowed, when an alkaline processing solution is permeated into said layer, to move into a layer containing the coupler so that said color developing agent may be brought into contact with said coupler. When the present color photosensitive material is used as a color photosensitive material for diffusion transfer, the couplers of the present invention may be used by incorporating them into a light-sensitive element and/or an image-receiving element of said photosensitive material, and particularly the present couplers are advantageously made present in the light-sensitive element. In the case of reversal development, the present color photosensitive material, after exposure, is developed with a black-and-white negative developer, followed by exposure to white light or treatment with a bath containing a fogging such as a boron compound, and is then color developed with an alkaline developer containing a color developing agent. In that case, the fogging agent may be incorporated into the alkaline developer containing the color developing agent. After color development, the photosensitive material is subjected to bleaching treatment with a bleaching solution containing, as an oxidizing agent, ferricyanide or ferric salt of aminopolycarboxylic acid and is then subjected to fixing treatment with a fixing solution containing a silver salt dissolving agent such as thiosulfate or the like, thereby to remove a silver image and the remaining silver halide and leave a dye image. It is also possible to effect bleach-fixing of the developed photosensitive material by the use of a one bath bleach-fixing solution containing an oxidizing agent such as the ferric salt of aminocarboxylic acid and a silver salt dissolving agent such as thiosulfate in place of the use of the bleaching solution and then of the fixing solution. It is also possible to subject the exposed photosensitive material to such treatments as pre-hardening, neutralizing, water-washing, stopping and stabilizing in combination with color development, bleaching, fixing or bleach-fixing treatment. A processing step wherein the color photosensitive material according to the present invention is particularly advantageously subjected to development is, for example, a sequence of steps of color development, if necessary, water-washing, bleach-fixing, water-washing, and stabilizing and drying, if necessary, and this processing step may be carried out at elevated temperature, for example, above 30° C. and within quite a short time.

Particularly useful color developing agents used in color developing the color photosensitive materials according to the present invention are primary phenylenediamines and aminophenols and derivatives thereof. Typical examples of the color developing agents include, for example, those as enumerated below.

N,N-Dimethyl-p-phenylenediamine, N,N-diethyl-p-phenylenediamine, n-carbamidomethyl-N-methyl-p-phenylenediamine, N-carbamidomethyl-N-tetrahydrofurfuryl-2-methyl-p-phenylenediamine, N-ethyl-N-carboxymethyl-2-methyl-p-phenylenediamine, N-carbamidomethyl-N-ethyl-2-methyl-p-phenylenediamine, N-ethyl-N-tetrahydrofurfuryl-2-methyl-p-aminophenol, 3-acetylamino-4-aminodimethylaniline, N-ethyl-N-$\beta$-methanesulfonamidoethyl-4-aminoaniline, N-ethyl-N-$\beta$-methanesulfonamidoethyl-3-methyl-4-aminoaniline, N-methyl-N-$\beta$-sulfoethyl-p-phenylenediamine, o-aminophenol, p-aminophenol, and salts of 5-amino-2-hydroxy-toluene with an inorganic acid such as hydrochloric or sulfuric acid or such organic acid as p-toluenesulfonic acid.

The color developing solution is incorporated, in addition to the color developing agent as aforesaid, with various additives. Principal examples of such additives include, for example, alkali agents such as hydroxides, carbonates or phosphates of alkali metals or ammonium, buffers such as acetic or boric acid, pH regulators, development accelerators, antifoggants, stain or sludge preventing agents, multi-layer effect promoting agents and stabilizing agents.

The bleaching agents used in bleaching treatment include ferricyanide such as potassium ferricyanide, bichromates, permanganates, hydrogen peroxide, bleaching powder, metal complex salts of aminopolycarboxylic acid such as ethylenediaminetetraacetic acid, nitrilotriacetic acid, iminodiacetic acid, etc., metal complex salts of polycarboxylic acid such as malonic acid, tartaric acid, malic acid, diglycolic acid, etc., and ferric chloride, and these bleaching agents may be used singly or, if necessary, in combination. The bleaching solution may be incorporated, if necessary, with various additives such as bleaching promotors and the like.

The fixing agents used in fixing treatment include thiosulfates such as sodium thiosulfate, ammonium thiosulfate, etc., cyanides, and urea derivatives, and the fixing solution may be incorporated, if necessary, with various additives such as fixing promotors and the like.

Color photosensitive materials in which the couplers of the present invention have been used may also be advantageously processed by the solution containing both a primary aromatic amine type color developing agent and an oxidizing agent capable of allowing a metallic silver image to undergo redox reaction.

When the above-mentioned color developing solution is used in developing the exposed color photosensitive material, the color developing agent is oxidized by means of the oxidizing agent and the oxidized color developing agent undergoes coupling with couplers to form a dye image. Such color developing solution is disclosed, for example, in Japanese-Laid-Open-to-Public Publication No. 9729/1973, and an oxidizing agent preferably suitable for the purpose includes cobalt complex salts having a coordination number of 6. Color photographic treatment involving the use of such color developing solution as mentioned above is particularly effectively applicable to processing of the so-called silver-saving type color photosensitive materials in which the amount of silver used is smaller than that of ordinary color photosensitive materials.

Particularly advantageously useful cobalt complex salts are those which contain ligands selected from the group consisting of ethylenediamine, diethylenetriamine, triethylenetetramine, amine, nitrate, nitrite, azide, chloride, thiocyanate, isothiocyanate, water and carbonate and which have (1) at least two ethylenediamine ligands, (2) at least five amine ligands or (3) at least one triethylenetetramine ligand. Particularly preferable cobalt complex salts are such complex salts as represented, for example, by the following formulas.

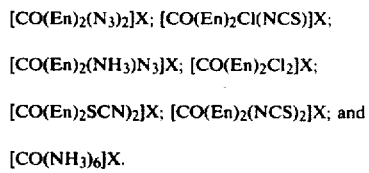

$[CO(En)_2(N_3)_2]X$; $[CO(En)_2Cl(NCS)]X$;

$[CO(En)_2(NH_3)N_3]X$; $[CO(En)_2Cl_2]X$;

$[CO(En)_2SCN)_2]X$; $[CO(En)_2(NCS)_2]X$; and $[CO(NH_3)_6]X$.

In the above formulas, En represents ethylenediamine and X represents at least one anion selected from chloride, bromide, nitrite, nitrate, perchlorate, acetate, carbonate, sulfite, sulfate, hydrochloride, thiocyanate, isothiocyanate and hydroxide. Most preferable complex salts are hexamine salts of cobalt, for example, chlorides, bromides, sulfites, sulfates, perchlorates, nitrites and acetates. The cobalt complex salt is generally used in a concentration ranging from about 0.1 to 50 g. per liter of the color developing solution.

Color photosensitive materials having contained therein the couplers of the present invention are advantageously applicable also to a photographic processing process which comprises developing the exposed color photosensitive material in a color developing solution containing an aromatic primary amine type color developing agent, preferably in the presence of such color developing agent as may be received during the color developing step into a photosensitive layer and as may be allowed to move into an amplifying bath, and then contacting the developed color photosensitive material with an amplifying solution containing the aforesaid oxidizing agent, for example, a cobalt complex salt having a coordination number of 6. Further, preferably usable as another oxidizing agent suitable for this purpose is an aqueous hydrogen peroxide solution disclosed, for example, in Japanese-Laid-Open-to-Public Publication No. 16023/1976. It is preferable that this amplifying solution be incorporated, in addition to the oxidizing agent, with a development inhibitor for silver halide and then used in processing color photosensitive materials. In such case, the amplifying step can be carried out under room light. According to this technique, it becomes possible to observe the progress of formation of dye and the dye formation can be suspended after a desired dye density has been attained. Preferable development inhibitors are water-soluble bromide compounds, such as potassium bromide, and heterocyclic compounds such as tetrazoles, azaindenes and triazoles containing no mercapto or ionic bromide group.

A concentration of the cobalt complex salt to be contained in the amplifying solution is generally about 0.2 to about 20 g/l, most preferably about 1 to about 15 g/l, and that of the aqueous hydrogen peroxide solution is generally about 0.01 to 10%, most preferably 0.5 to 10%. In case the water-soluble bromide compound is used as a development inhibitor in the amplifying solution, said compound is contained therein generally in an amount of about 1 to about 40 g/l. The development inhibitor consisting of a compound having a heterocyclic structure, on the other hand, is used usually in a concentration of about 0.01 to about 3 g/l. The amplifying solution, when used, is ordinarily adjusted to pH 6-14, preferably pH 8-12.

Further, if necessary, the amplifying solution may be incorporated with development accelerators, stabilizers, water-softening agents, thickeners, surface active agents and the like additives in addition to the above-mentioned development inhibitors.

The present invention is illustrated below with reference to examples, but embodiments of the invention are not limited by these examples.

EXAMPLE 1

Couplers (M-3), (M-5), (M-7) and (M-9) of the present invention, comparative couplers A, B and C, and a combination of the comparative coupler A and a fading inhibitor were individually dissolved together with 120 mg of Hq-1 in a mixture of dibutyl phthalate (DBP) and ethyl acetate (EA) in the manner as shown in Table 1—1. Each of the resulting solutions was incorporated into a mixture comprising 100 ml of sodium dialkylnaphthalenesulfonate (Alkanol B; a product produced and sold by Du Pont Co.) and 400 ml of a 5% aqueous gelatin solution. The resulting mixture was emulsified and dispersed by means of a colloid mill to obtain a coupler dispersion.

Subsequently, each of the coupler dispersions obtained in the above manner was incorporated into 1000 ml of a green-sensitive silver chlorobromide emulsion (containing 40 mole% of silver chloride), and the emulsion, to which was added 20 ml of a 1% aqueous solution of 1,2-bis(vinylsulfonyl)ethane as a film hardener, was coated on a polyethylene-coated paper and then dried. There were obtained samples of color photosensitive materials numbered from 1 to 8 as shown in Table 1—1.

After exposure to light through an optical wedge, the samples were individually processed at 30° C. according to the following procedure to obtain samples having formed thereon their respective color images. Processing step:

Color development (3 min. 30 sec.)→Bleach-fixing (1 min. 30 sec.)→water-washing (2 min.)→stabilizing (1 min.)→drying.

Processing solutions used were those having the following respective compositions. Composition of the color developing solution:

| | |
|---|---|
| Benzyl alcohol | 5.0 g |
| Sodium hexametaphosphate | 2.5 g |
| Anhydrous sodium sulfite | 1.9 g |
| Sodium bromide | 1.4 g |
| Potassium bromide | 0.5 g |
| Borax (Na$_2$B$_4$O$_7$ . 10 H$_2$O) | 39.1 g |
| N-Methyl-N-β-methanesulfonamidoethyl-4-aminoaniline sulfate | 5.0 g |

Water to make 1 liter and adjust the pH to 10.30 with sodium hydroxide. Composition of the bleach-fixing solution:

| | |
|---|---|
| Ammonium iron ethylenediaminetetraacetate | 61.0 g |
| Diammonium ethylenediaminetetraacetate | 5.0 g |
| Ammonium thiosulfate | 124.5 g |
| Sodium metabisulfite | 13.3 g |
| Anhydrous sodium sulfite | 2.7 g |

Water to make 1 liter and adjust to pH 6.5 with ammonia water. Composition of the stabilizing solution:

| | |
|---|---|
| Glacial acetic acid | 20 ml |

Add 800 ml of water and adjust to pH 3.5-4.0 with sodium acetate and then water to make 1 liter.

Each of the samples thus processed was measured in speed, gamma, fog and maximum density. In order to investigate light fastness of each sample, moreover, a density after irradiation for 100 hours by means of a Xenon fade-o-meter as measured in terms of residual dye ratio, when the initial density was 1.0, was obtained and, further, a density after the irradiation in the unexposed area (Dmin) of each sample as measured in terms of Y-stain increasing ratio represented by percent was obtained. The results obtained were as shown in Table 1-2.

In the table, the speed was represented by a relative value as measured by assuming as 100 the speed of the sample in which the comparative coupler A was used singly.

Table 1-1

| Sample | Exemplified compound | Amount of compound added | DBP (g) | EA (g) |
|---|---|---|---|---|
| 1 | (M-3) | 35.5 | 36 | 100 |
| 2 | (M-5) | 37.0 | 37 | " |
| 3 | (M-7) | 39.5 | 40 | " |
| 4 | (M-9) | 34.0 | 34 | " |
| 5 | Comparative coupler A | 35.5 | 36 | " |
| 6 | Comparative coupler A Fading inhibitor | 35.5 10.5 | 36 | " |
| 7 | Comparative coupler B | 40.0 | 40 | " |
| 8 | Comparative coupler C | 37.0 | 37 | " |

Table 1-2

| Sample | Speed | Fog | Gamma | Maximum density | Residual dye ratio | Y-stain increasing |
|---|---|---|---|---|---|---|
| 1 | 102 | 0.02 | 2.4 | 2.8 | 82 | 450 |
| 2 | 105 | 0.02 | 2.3 | 2.7 | 89 | 435 |
| 3 | 101 | 0.02 | 2.4 | 2.7 | 91 | 405 |
| 4 | 100 | 0.01 | 2.3 | 2.8 | 86 | 440 |
| 5 | 100 | 0.03 | 2.5 | 2.8 | 55 | 1200 |
| 6 | 99 | 0.03 | 2.4 | 2.6 | 64 | 760 |
| 7 | 92 | 0.02 | 2.3 | 2.6 | 78 | 600 |
| 8 | 100 | 0.03 | 2.4 | 2.8 | 64 | 845 |

The comparative couplers and fading inhibitor used were those having the following respective structures.

Comparative coupler A:

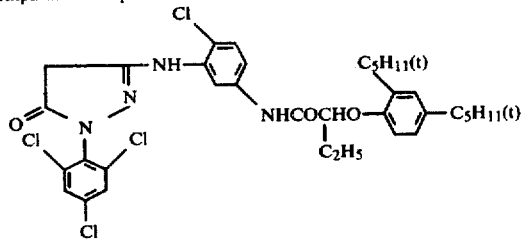

Comparative coupler B:

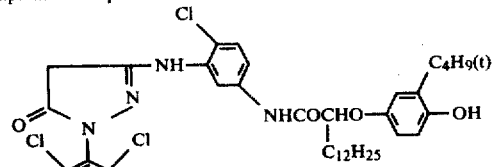

(A compound disclosed in U.S. Pat. No. 3,519,429)

Comparative coupler C:

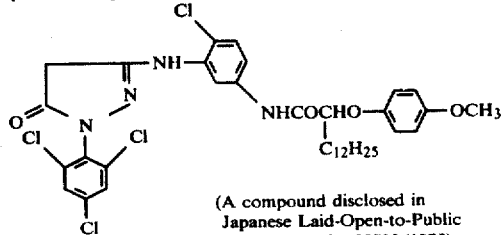

(A compound disclosed in Japanese Laid-Open-to-Public Publication No. 20723/1975)

Fading inhibitor:

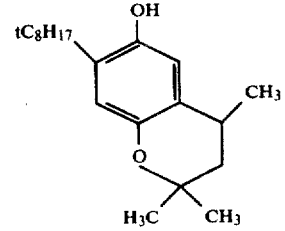

(A compound disclosed in U.S. Pat. No. 3,432,300)

From the results shown in Table 1-2, it is understood that the couplers of the present invention have excellent fading inhibition effect as well as Y-stain prevention effect as compared with the known couplers.

Further, the present couplers were excellent not only in solubility in such high boiling solvent as DBP but also in stability to dispersions in which they had been dispersed.

Furthermore, similar results were obtained even when Hq-1 was omitted and instead Hq-3, Hq-5, Hq-10, Hq-13, Hq-17 and Hq-20 were used respectively.

EXAMPLE 2

Couplers (Y-7) and (Y-9) and comparative couplers D and E which will be illustrated later were individually dissolved together with 150 mg of Hq-1 in a solvent shown in Table 2-1. Each of the resulting solutions was incorporated into 500 ml of a 5% aqueous gelatin solution containing 3.0 g. of sodium dodecylbenzenesulfonate, and the mixture was then dispersed by means of a homogenizer to obtain a dispersion. The dispersion thus obtained was incorporated into 1000 ml of a blue-sensitive silver chlorobromide emulsion (containing 10 mole% of silver chloride), and the emulsion to which was added 10 ml of a 2% methanol solution of N,N',N''-trisacryloylhexahydro-S-triazine as a film hardener was coated on a subbed polyethylene terephthalate film and then dried to obtain a sample. In this manner, there were prepared samples of color photo-sensitive materials numbered from 1 to 4 as shown in Table 2-1.

In the case of the sample No. 2, the amount of silver used was one half of that used in other samples, because the present coupler (Y-9) was a so-called 2-equivalent coupler.

The samples thus prepared were individually processed according to the following processing step. Processing step:

Color development (at 30° C. for 3 min. 30 sec.)→ stopping→first fixing→washing (10 min.)→bleaching (at 20° C. for 5 min.)→washing (at 20° C. for 5 min.)→second fixing (at 20° C. for 5 min.)→washing (at 20° C. for 25 min.)→drying.

The color developing solution used had the same composition as in the solution used in Example 1 and the stopping and the first fixing were conducted according to the usual procedure. The bleaching solution and second fixing solution used were those having the respective compositions mentioned below. Composition of the bleaching solution:

| Potassium ferricyanide | 100 g |
|---|---|
| Potassium bromide | 50 g |
| Water to make | 1 liter |

Composition of the second fixing solution:

| Sodium thiosulfate (pentahydrate) | 250 g |
|---|---|
| Anhydrous sodium sulfite | 12 g |
| Potassium alum | 15 g |
| Acetic acid | 12 g |
| Water to make | 1 liter |

The samples thus processed were individually tested in the same manner as in Example 1, except that fog after the irradiation was measured but the measurement of Y-stain increasing ratio was omitted. The results obtained were as shown in Table 2-2.

In Table 2-2, the speed was represented by a relative value as measured by assuming as 100 the speed of the sample in which the comparative coupler D was used.

Table 2-1

| Sample | Exemplified coupler | Amount of coupler added | TCP (g) | EA (g) |
|---|---|---|---|---|
| 1 | (Y-7) | 54 | 54 | 110 |
| 2 | (Y-9) | 73 | 73 | " |
| 3 | Comparative coupler D | 57 | 57 | " |
| 4 | Comparative coupler E | 67 | 67 | " |

In the above table, TCP represents tricresyl phosphate.

Table 2-2

| Sample | Speed | Gamma | Fog | Maximum density | Residual dye ratio | Fog after irradiation |
|---|---|---|---|---|---|---|
| 1 | 102 | 2.0 | 0.25 | 2.3 | 89 | 0.22 |
| 2 | 103 | 2.1 | 0.22 | 2.4 | 90 | 0.12 |
| 3 | 100 | 2.0 | 0.36 | 2.3 | 80 | 0.32 |
| 4 | 110 | 2.0 | 0.42 | 2.4 | 30 | 0.37 |

The comparative couplers used had the following structures.

Comparative coupler D:

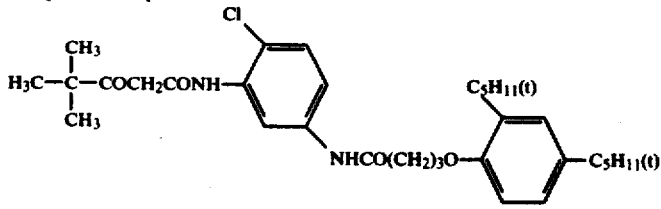

(A compound disclosed in U.S. Pat. No. 3,265,506)

Comparative coupler E:

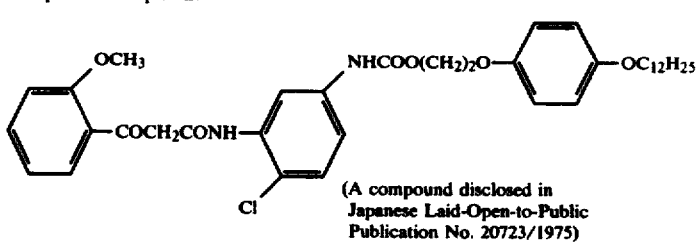

(A compound disclosed in Japanese Laid-Open-to-Public Publication No. 20723/1975)

From the results shown in Table 2-2, it is understood that the yellow couplers of the present invention also have excellent light fastness as compared with the conventionally known couplers and, at the same time, the present couplers have less formation of initial fog, cause no substantial damage in photographic properties of the resulting color photosensitive materials, have excellent solubility even in a high boiling solvent as TCP, and are excellent in stability to the dispersions in which they had been dispersed. Similar results were obtained even when Hq-1 was omitted and instead Hq-3, Hq-5, Hq-10, Hq-13, Hq-17 and Hq-20 were respectively used.

EXAMPLE 3

On a polyethylene-coated paper were coated successively from the side of the support to obtain a sample of color photosensitive material (sample No. 1). First layer: A blue-sensitive silver halide emulsion layer comprising a silver chlorobromide emulsion containing 10 mole% of silver chloride, said emulsion comprising 400 g of gelatin per mole of silver halide, being sensitized by using $2.5 \times 10^{-4}$ mole, per mole of silver halide, of a sensitizing dye having the following structure, containing $2 \times 10^{-1}$ mole, per mole of silver halide, of the present yellow coupler (Y-9) being dissolved and dispersed in DBP, and being coated on the support so that the amount of silver becomes 400 mg/m².

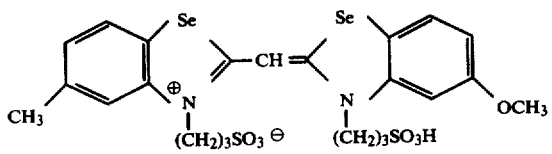

Second layer: A gelatin layer being coated on the first layer so as to have a dry film thickness of 1μ. Third layer: A green-sensitive silver halide emulsion layer comprising a silver chlorobromide emulsion containing 40 mole% of silver chloride, said emulsion containing 500 g. of gelatin per mole of silver halide, being sensitized by using $2.5 \times 10^{-4}$ mole, per mole of silver halide, of a sensitizing dye having the following structure, containing $2 \times 10^{-1}$ mole, per mole of silver halide, of the present coupler (M-7) dissolved and dispersed in TCP, and being coated on the third layer so that the amount of silver is 500 mg/m².

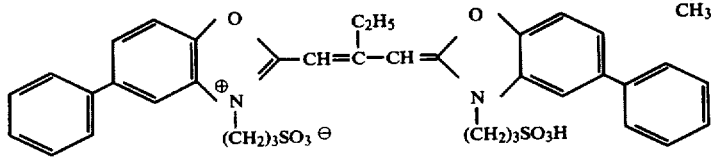

Fourth layer: A gelatin layer containing 30 mg/m² of Hq-1 and 0.7 g/m² of 2-(2'-hydroxy-3',5'-di-t-butylphenyl)-benzotriazole dissolved and dispersed in DBP and being coated on the third layer so as to have a dry film thickness of 1μ. Fifth layer: A red-sensitive silver halide emulsion layer comprising a silver chlorobromide emulsion containing 20 mole% of silver chloride, said emulsion containing 500 mg of gelatin per mole of silver halide, a sensitizing dye having the following structure, containing $2 \times 10^{-1}$ mole, per mole of silver halide, of a cyan coupler having the following structure, and being coated on the fourth layer so that the amount of silver becomes 500 mg/m².

Structure of the sensitizing dye:

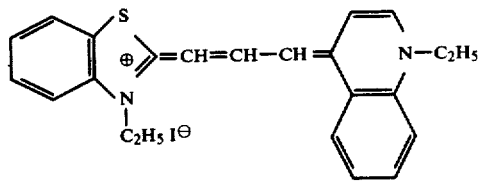

Structure of the cyan coupler:

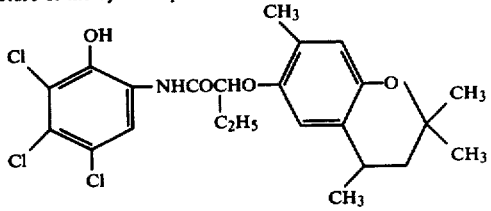

Sixth layer: A gelatin layer being coated on the fifth layer so as to have a dry film thickness of 1μ.

The silver halide emulsions respectively used in the above-mentioned photosensitive layers were individually prepared according to the procedure described in Japanese Patent Publication No. 7772/1971, and then subjected individually to chemical sensitization by the use of sodium thiosulfate pentahydrate and incorporated individually with 4-hydroxy-6-methyl-1,3,3a,7-tetrazaindene as a stabilizer, tetrakis-(vinylsulfonylmethyl)methane as a film hardener and saponin as a coating aid.

Subsequently, sample No. 2 was prepared in the same manner as above, except that there were used, in an equimolar amount in each case, the comparative yellow coupler D of Example 2 in the first layer in place of the present coupler (Y-9), the comparative magenta coupler B of Example 1 in the third layer in place of the present coupler (M-7), and a coupler of the following structure in the fifth layer in place of the cyan coupler used in said layer.

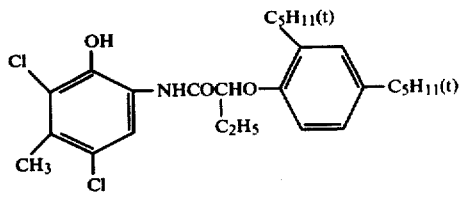

The samples prepared in the above manner were individually exposed through optical wedges to blue light, green light and red light, and then processed according to the processing step employed in Example 1. Thereafter, the processed samples were irradiated for 100 hours by means of a Xenon fade-o-meter and then measured for residual dye ratio and Y-stain increasing ratio to obtain the results as shown in Table 3, wherein the measured values were expressed in the same manner as in Table 1-2 of Example 1.

Table 3

| Sample No. | Residual dye ratio (%) | | | Y-stain increasing ratio (%) |
|---|---|---|---|---|
| | Yellow | Magenta | Cyan | |
| 1 | 94 | 96 | 95 | 140 |
| 2 | 90 | 88 | 95 | 280 |

From the results shown in Table 3, it is understood that the sample containing the couplers of the present invention shows excellent light fastness even when used in a multi-coated color photosensitive material, as compared with the sample containing the known couplers.

Further, results similar to those in this example were obtained even when Hq-1 used in this example was omitted and instead Hq-3, Hq-5, Hq-10, Hq-13, Hq-17 and Hq-20 were used respectively.

What we claim is:

1. A color photosensitive material comprising a support and a silver halide photosensitive layer which material comprises a coupler represented by the following formulas (IV), (V) or (VI) having therein a group represented by formula (I), said coupler being capable of forming an azomethine dye on coupling with the oxidation product of an aromatic primary amine developer:

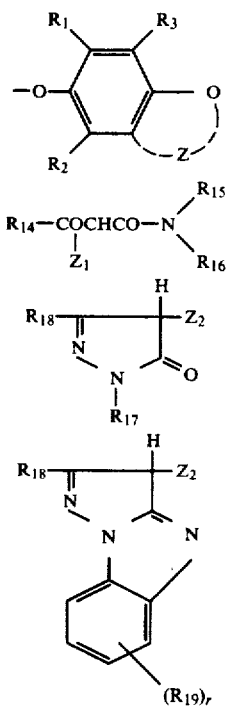

wherein $R_1$, $R_2$ and $R_3$ individually represent hydrogen, halogen, alkyl, alkenyl, cycloalkyl, aryl, alkoxy, alkenyloxy, cycloalkoxy, aryloxy, alkylthio, alkenylthio, cycloalkylthio, arylthio, acyl, acylamino, diacylamino, acyloxy, sulfonamido, or alkoxycarbonyl; and Z represents an atomic group necessary for forming a chroman or coumaran ring; $R_{14}$ represents alkyl, pinanyl, bornyl, norbornyl, cycloalkyl, aryl, pyridyl, pyrazinyl, pyridazyl, quinonyl, thienyl, furanyl, thiazolyl, benzothiazolyl, oxazolyl, piperidyl, pyrrolyl, pyrrolinyl, tetrazolyl, thiazinyl, morpholino, furyl, benzooxazolyl, imidazolyl, benzoimidazolyl group; $R_{15}$ and $R_{16}$ represent individually hydrogen, alkyl or aryl; and $Z_1$ represents h hydrogen or a split-off group selected from the group consisting of halogen, —OZ', —OCOZ', —SZ', —OCONHZ', —OSO$_2$NHZ', —NHCOZ', —NHSO$_2$Z', —NHZ' (in which Z' represents hydrogen, alkyl, aryl or a heterocyclic ring), —SO$_3$H, —SCN, azo and a heterocyclic ring containing nitrogen, oxygen and/or sulfur; $R_{17}$ represents hydrogen, alkyl, alkenyl, norbornyl, cycloalkyl, aryl, pyridyl, pyrazinyl, pyridazyl, quinonyl, a thienyl, furyl, thiazinyl, morpholino, tetrazolyl, benzothiazolyl, thiazolyl, benzoxazolyl, oxazolyl, benzimidazolyl, imidazolyl group, piperidyl, pyrrolyl, pyrrolinyl, naphthoxazolyl; and $R_{18}$ represents alkyl, aryl, alkenyl, norbornyl, alkoxy, amino, ureido, pyridyl, pyrazinyl, pyridazyl, quinonyl, thienyl, furyl, thiazinyl, morpholino, tetrazolyl, benzothiazolyl, thiazolyl, benzoxazolyl, oxazolyl, benzimidazolyl, imidazolyl, piperidyl, pyrrolyl, pyrrolinyl, and napthoxazolyl; $R_{19}$ represents hydrogen, halogen, alkyl, alkoxy, acylamino, carbamoyl or sulfamoyl; r represents 1–4; and $Z_2$ represents $Z_1$.

2. The color photosensitive material according to claim 1 wherein the coupler is represented by formula (IV) and provided that at least one of $R_{14}$, $R_{15}$, $R_{16}$, and $Z_1$ represents the group of

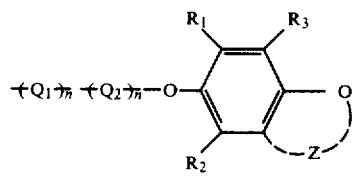

in which n is 0 or 1 and m is 0 or 1 where $Q_1$ is alkylene, cycloalkylene, arylene, a divalent group in which at least one alkylene group is bonded to at least one arylene group or a divalent heterocyclic ring containing nitrogen and/or sulfur, and $Q_2$ is —CO—, —CS—, —SO$_2$—, —CONH—, —SO$_2$NH—, —NHCO—, —NHSO$_2$—

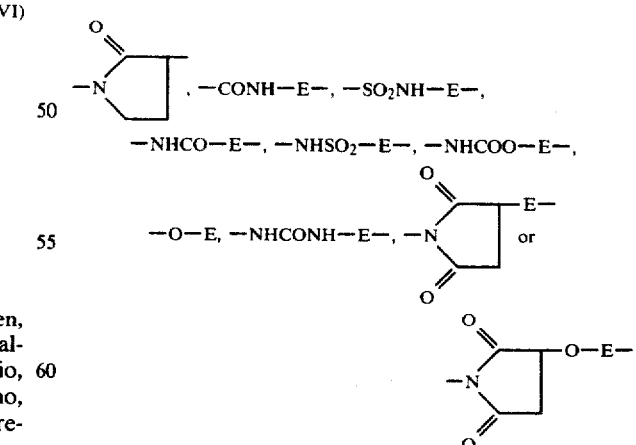

wherein E represents an alkylene group.

3. The color photosensitive material according to claim 2 wherein the coupler is represented by formula (IV-a) or (IV-b);

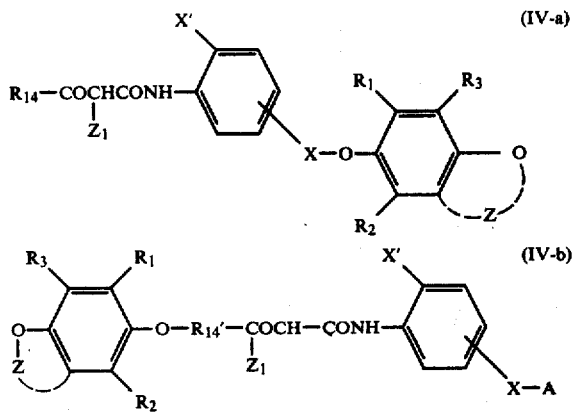

wherein X represents —NHCO—R"—, —NHSO$_2$—R"—, —COO—R'—, —NHCONH—R'—, —CONH—R'—, —SO$_2$NH—R' or

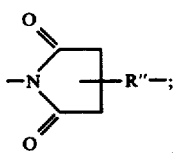

R' represents alkylene, arylene or a divalent heterocyclic ring containing nitrogen and/or sulfur; R" represents a simple bond or R'; R'$_{14}$ represents alkylene, arylene or a divalent heterocyclic ring containing nitrogen and/or sulfur; A represents alkyl or aryl; and X' represents halogen, alkoxy or aryloxy.

4. The color photosensitive material according to claim 1 wherein the coupler is represented by formula (V) or (VI) and provided that at least one of R$_{17}$, R$_{18}$, R$_{19}$, and Z$_2$ represents

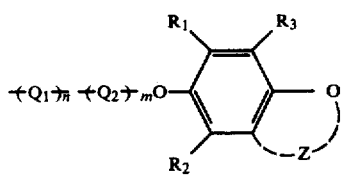

in which n is 0 or 1 and m is 0 or 1, where Q$_1$ is alkylene, cycloalkylene, arylene, a divalent group in which at least one alkylene group is bonded to at least one arylene group, or a divalent heterocyclic ring, containing nitrogen and/or sulfur, and Q$_2$ is

—CO—, —CS—, —SO$_2$—, —CONH—, —SO$_2$NH—,

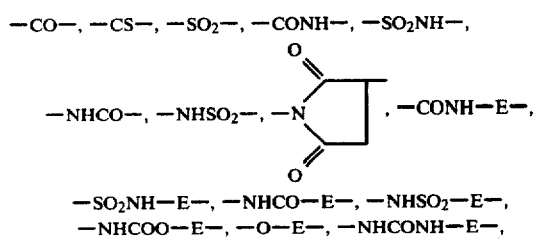

—SO$_2$NH—E—, —NHCO—E—, —NHSO$_2$—E—, —NHCOO—E—, —O—E—, —NHCONH—E—,

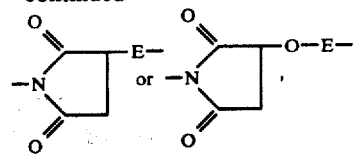

where E represents an alkylene group.

5. A color photosensitive material according to claim 1 wherein the group of formula [I] is represented by the following formulas [II] or [III]:

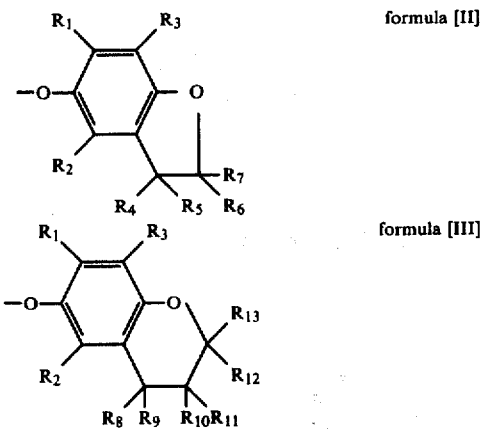

wherein R$_4$, R$_5$, R$_6$, R$_7$, R$_8$, R$_9$, R$_{10}$, R$_{11}$, R$_{12}$ and R$_{13}$ individually represent hydrogen, halogen, alkyl, alkenyl, cycloalkyl, aryl, alkoxy, alkenyloxy, cycloalkyloxy, aryloxy, alkylthio, alkenylthio, cycloalkylthio, arylthio, or amino, and R$_{12}$ and R$_{13}$ can have togethwer cyclized to form a hydrocarbon nucleus.

6. A color photosensitive material according to claim 1 wherein R$_1$, R$_2$ and R$_3$ individually represent hydrogen, alkyl or cycloalkyl.

7. A color photosensitive material according to claim 6 wherein R$_1$, R$_2$ and R$_3$ individually represent hydrogen or alkyl.

8. A color photosensitive material according to claim 7 wherein R$_1$ represents a lower alkyl.

9. A color photosensitive material according to claim 8 wherein R$_1$ represents methyl.

10. A color photosensitive material according to claim 7 wherein R$_2$ and R$_3$ individually represent hydrogen.

11. A color photosensitive material according to claim 5 wherein R$_4$, R$_5$, R$_6$, R$_7$, R$_8$, R$_9$, R$_{10}$, R$_{11}$, R$_{12}$ and R$_{13}$ individually represent hydrogen, halogen, alkyl having 1-22 carbon atoms or cycloalkyl, and R$_{12}$ and R$_{13}$ may cyclize together to form a 5- or 6-membered saturated hydrocarbon nucleus.

12. A color photosensitive material according to claim 4 wherein the coupler is represented by the formula [V].

13. A color photosensitive material according to claim 12 wherein R$_{17}$ represents phenyl having a substituent or substituents in at least one of the ortho positions, the substituent or substituents being selected from alkyl, alkoxy and halogen.

14. A color photosensitive material according to claim 12 wherein the coupler is represented by the following formula [V-a] or [V-b]

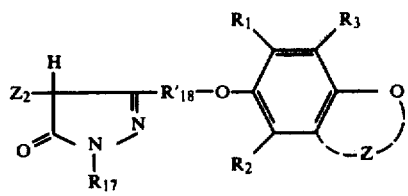
formula [V-a]

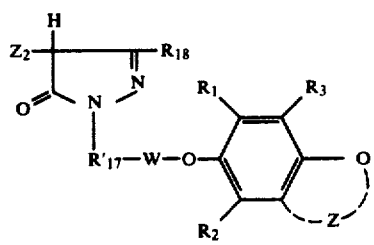
formula [V-b]

wherein R′$_{18}$ represents

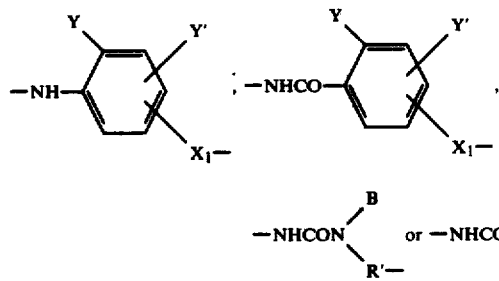

Y represents hydrogen, halogen, alkyl or alkoxy; Y′ represents Y; B represents hydrogen or an alkyl group; X$_1$ represents

—NHCO—R′—, —NHSO$_2$—R′—, —CONH—R′—,

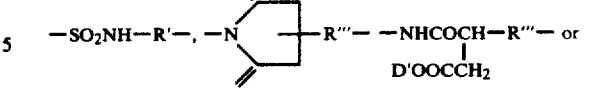

—NHCOCH$_2$;
   |
   D′OOCCH—R′′′—

R′′′ represents a simple bond, —O—R′—, —S—R′—, —SO$_2$R′— or —ND—R′—; D represents hydrogen, alkyl, aryl or acyl group; D′ represent alkyl, R′$_{17}$ represents alkylene or arylene; and W represents a simple bond, —NH—R′—, —NHCO—R′—, —NHCONH—R′—, —O—R′— or —CONH—R′—.

15. A color photosensitive material according to claim 14 wherein R′$_{17}$ represents a phenylene group.

16. A color photosensitive material according to claim 14 wherein R′$_{17}$ represents halogen-substituted phenylene.

17. A color photosensitive material according to claim 14 wherein R′$_{18}$ represents

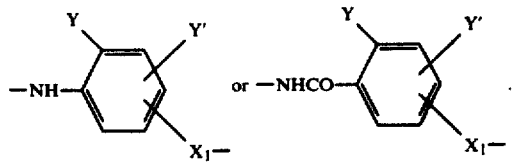

18. A color photosensitive material according to claim 17 wherein X$_1$ represents —NHCO—R′— or —NHSO$_2$—R′— and R′ represents alkylene.

19. A color photosensitive material according to claim 17 wherein R′$_{18}$ represents

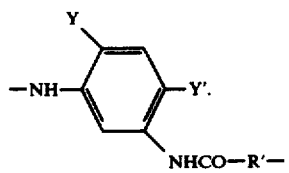

* * * * *